United States Patent [19]

Blanco et al.

[11] Patent Number: 5,260,882

[45] Date of Patent: Nov. 9, 1993

[54] PROCESS FOR THE ESTIMATION OF PHYSICAL AND CHEMICAL PROPERTIES OF A PROPOSED POLYMERIC OR COPOLYMERIC SUBSTANCE OR MATERIAL

[75] Inventors: Mario Blanco, Jeffersonville, Pa.; Thomas H. Pierce, Lawrenceville, N.J.

[73] Assignee: Rohm and Haas Company, Philadelphia, Pa.

[21] Appl. No.: 636,629

[22] Filed: Jan. 2, 1991

[51] Int. Cl.[5] .................. G06F 15/60; G06F 15/20
[52] U.S. Cl. .................................. 364/499; 364/496; 364/578
[58] Field of Search ............... 364/496, 497, 499, 578, 364/518–522; 436/86, 89; 935/87; 395/100, 119, 920, 932

[56] References Cited

U.S. PATENT DOCUMENTS

| | | | |
|---|---|---|---|
| 4,486,657 | 12/1984 | Heckel | 364/900 |
| 4,704,692 | 11/1987 | Ladner | 364/496 |
| 4,736,308 | 4/1988 | Heckel | 364/518 |
| 4,744,028 | 5/1988 | Karmarkar | 364/402 |
| 4,853,871 | 8/1989 | Pantoliano et al. | 364/496 |
| 4,855,931 | 8/1989 | Saunders | 364/499 |
| 4,881,175 | 11/1989 | Ladner | 364/496 |
| 4,908,773 | 3/1990 | Pantoliano et al. | 364/496 |
| 4,939,666 | 7/1990 | Hardman | 364/496 |
| 5,008,831 | 4/1991 | Feldman | 364/496 |
| 5,019,998 | 5/1991 | Cowan et al. | 364/578 X |
| 5,025,388 | 6/1991 | Cramer, III et al. | 364/496 |
| 5,065,336 | 11/1991 | Buchelli | 364/499 |

OTHER PUBLICATIONS

Puleo, A. C., Muruganandam, N., Paul, D. R., "Gas Sorption and Transport in Substituted Polystyrenes", J. of Polymer Science Part B: Polymer Physics, 1989, 27, 2385–2406 (1989).

Molecular Silverware. I. General Solutions to Excluded Volume Constrained Problems, Mario Blanco, Journal of Computational Chemistry, accepted for publication Jul. 3, 1990.

MacroModel–An Integrated Software System for Modeling Organic and Biorganic Molecules Using Molecular Mechanics, by Fariborz Mohamadi et al, Department of Chemistry, Havemeyer Hall, Columbia University, New York, N.Y. 10027.

Statistical Mechanics of Chain Molecules, Paul J. Flory, J. G. Jackson-C. J. Wood Professor of Chemistry, Stanford University, Interscient Publishers.

Alfrey, T. Jr., & C. C. Price; J of Polymer Science, 2, 101 (1947).

(List continued on next page.)

Primary Examiner—Kevin J. Teska
Attorney, Agent, or Firm—Connolly & Hutz

[57] ABSTRACT

A process for estimation of properties utilizing experimental information using constraint determined by chemical kinetics, statistical thermodynamics and molecular mechanics including experimental information on proposed polymeric or copolymeric substances of large molecules for the estimation of the physical properties of the substances by

- first defining the substances molecular chemical composition,
- second, estimating properties of the molecular chemical composition when 3-dimensionally folded,
- third, forming the composition into a polymeric cluster,
- fourth, estimating the physical properties of the polymeric cluster, and finally preparation of the polymeric substances having the properties as estimated.

The present invention overcomes the "multiple stable minimum" which is associated with prior polymer modeling approaches of large molecules.

17 Claims, 27 Drawing Sheets

OTHER PUBLICATIONS

Blanco, M., J. of Computational Chemistry, "The Modeling of Non-Crystalline Condensed Phases-General Solutions to Excluded Volume Constrained Problems'-'-Jul. 3, 1990.

Clarke, J. "New Opportunities for Modelling Polymers", Chemistry and Industry, 780-786, Dec. 3, 1990.

Flory, P. J., "Spatial Configuration of macromolecular Chains", Nobel Lecture, Dec. 11, 1974, Selected Works of Paul J. Flory, Mandelken, Mark, Suter, Yoon Eds. Stanford Univ. Press, V. 1. (5), 1985.

Jean Guillot (Makromol. Chem., Macromol. Symp., 35/36, 269-289 (1990).

Skeist, I.: J. of the American Chem. Soc., 68, 1781 (1946).

Sorensen, R. A., Liau, W. B., Boyd, R. H., "Prediction of Polymer Structures and Properties":, Macromolecules, 21, 194-199, 1988.

Walling and Briggs; J. of the American Chem. Society 67, 17741 (1945).

INVERSE FREE VOLUME 1/Vf

PROCESS FOR THE ESTIMATION OF PHYSICAL AND CHEMICAL PROPERTIES OF A PROPOSED POLYMERIC OR COPOLYMERIC SUBSTANCE OR MATERIAL

BACKGROUND FOR THE INVENTION

1. Field Of The Invention

The present invention relates to a process for the estimation and development of proposed chemical polymeric or copolymeric materials or substances. In particular, this invention utilizes chemical kinetics, statistical thermodynamics and molecular mechanics, including experimental information, in the creation of a more exacting molecular model.

2. Description Of The Related Art

In the art of modeling polymers, a set of current techniques involve the use of molecular mechanics or molecular dynamics. Both methods have proven to be very useful in accounting for the conformational energetics and properties of polymer molecules. These methods are based on the premise that a molecule can be simulated by empirical transferable energy functions that represent bond stretching, bending, and twisting as well as more distant non-bonded or steric interactions. Electrostatic forces are included when appropriate. A stable conformation is found as a minima in the total energy function. This process has reached a high state of development and has had many successes. See Sorensen, R. A., Liau, W. B., Boyd, R. H., "Prediction of Polymer Structures and Properties", Macromolecules, 21, 194–199, 1988. However, in contrast to the handful of stable minima found in small molecules, which are usually indicative of compounds used in the pharmaceutical or agricultural chemical industries, large polymer molecules have a great number of such "stable minima". Consequently, prior art modeling techniques were unable to effectively model large and complex polymers.

Moreover, except for a few crystalline homopolymers, past polymer modeling approaches have always divorced the specific chemical molecular structure, such as atom connectivity and atomic coordinates of the polymer, from the chemical calculations. It is both important and desirable to include information about the chemical molecular structure because a large class of commercial polymers contain more than one monomer type. These polymers are often prepared with great regard for the intrinsic differences in the reaction kinetics of the various monomers.

It is an object of the present invention to provide a process for modeling polymers which would be effective for large molecules overcoming the "multiple stable minima" problem, as well as combining the specific chemical molecular structure in the calculation of physical and chemical properties. These large molecules are polymeric or copolymeric substances or materials which can be used in plastics, packaging materials, optical disk materials, barrier membranes, adhesives, viscosity improvers, dispersants, electronic chemicals, coatings, or synthetic biopolymers. Examples of plastics include polymer blend compatibilizers, high-temperature plastics, thermoplastic, elastomeric, amorphous, crystalline or liquid crystalline polymers, polymer blends, and barrier membranes for bio-separation materials. FIG. 1 is a computer generated three-dimensionally folded full molecular structure using the process of the instant invention. All atoms are included for an atactic methyl methacrylate (MMA) chain, the main constituent in PLEXIGLAS ®, a polymer sold by Rohm & Haas Company.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

SUMMARY OF THE INVENTION

To achieve the foregoing objects, and in accordance with the purpose of the invention as embodied and broadly described herein, there is provided a process for the estimation of physical properties of a proposed polymeric or copolymeric substance or material comprising the steps of:

(a) defining or determining the proposed polymeric or copolymeric substance or material's molecular chemical composition through estimation of individual polymer chain chemical composition;

(b) estimating properties of the molecular chemical composition when 3-dimensionally folded;

(c) assembling the resulting 3-dimensionally folded molecular chemical composition into a polymeric of copolymeric cluster; and d) estimating the physical properties of the resulting polymeric of copolymeric cluster.

In various preferred embodiments, step (a) involves estimating the molecular chemical composition as a function of conversion using kinetics rate theory; step (b) uses numerical methods based upon statistical thermodynamics such as Global Growth, In Situ Growth, Simple Phantom and Conditional Phantom Growth; step (c) uses molecular excluded volume constraints determined by vector geometry, and iterative use of numerical methods such as Global Growth, In Situ Growth, Simple Phantom, and Conditional Phantom Growth; and step (d) involves calculation of molecular energy expressions, or quantitative structure-property relationships such as thermal properties, optical properties, diffusion properties, and mechanical properties or a combination thereof.

The instant process utilizes experimental information from chemical kinetics (reactivity ratios) and statistical thermodynamics (Boltzmann probabilities) to add physical as well as chemical constraints in the modeling of the polymer. As a result of the use of this invention, the modeling of polymers will rely less heavily upon the intuition and expertise of the polymer modeler and more on the experimental information at hand.

BRIEF DESCRIPTION OF THE DRAWINGS

The accompanying drawings, which are incorporated in and constitute a part of the specification, illustrate aspects of the invention and, together with the general description given above and the detailed description of the invention given below, serve to explain the principles of the invention.

FIG. 11. is a computer generated picture of the resulting polymer wherein the starting materials were a 50:50 mixture of methyl acrylate (MA) and styrene (STY) in accordance with Example 1, case a;

FIG. 12. is a computer generated picture of the resulting polymer wherein the starting materials were a 50:50 mixture of methyl acrylate (MA) and styrene (STY) at 0% conversion in accordance with Example 1, case a;

FIG. 13. is a computer generated picture of the resulting polymer wherein the starting materials were a 50:50 mixture of methyl acrylate (MA) and styrene (STY) at 20% conversion in accordance with Example 1, case a;

FIG. 14. is a computer generated picture of the resulting polymer wherein the starting materials were a 50:50 mixture of methyl acrylate (MA) and styrene (STY) at 40% conversion in accordance with Example 1, case a;

FIG. 15. is a computer generated picture of the resulting polymer wherein the starting materials were a 50:50 mixture of methyl acrylate (MA) and styrene (STY) at 60% conversion in accordance with Example 1, case a;

FIG. 16. is a computer generated picture of the resulting polymer wherein the starting materials were a 50:50 mixture of methyl acrylate (MA) and styrene (STY) at 80% conversion in accordance with Example 1, case a;

FIG. 17. is a computer generated picture of the resulting polymer wherein the starting materials were a 50:50 mixture of methyl acrylate (MA) and styrene (STY) at 99% conversion in accordance with Example 1, case a;

THE INVENTION

Applicants have succeeded in developing a process which combines a summary of molecular mechanics calculations on a variety of stable minima conformations, in the form of statistical weights or probabilities, and reaction kinetic expressions. Further, because the molecular structure is known at all points in the process, it is possible to estimate the polymer's physical properties by employing quantitative structure property relationships or more advanced methods based on the spatial distribution and energetics of all the atoms in the polymer. Because many properties, including mechanical and diffusion, are a function of clusters of polymer molecules instead of isolated molecules, the present process provides methods whereby the clusters are assembled.

Polymer Chemical Composition Further Composition

In a polymerization system containing two or more monomers, or monomer types (defined as different conformations of a monomer), the composition of the polymer being formed usually varies as a function of conversion. See Skeist, I.; J. of the American Chemical Society, 68, 1781 (1946) which generalized the work of Alfrey, T. Jr., and C. C. Price; J. of Polymer Science, 2, 101 (1947) and Walling and Briggs; J. of the American Chemical Society, 67, 17741 (1945) and formulated general equation to describe the change of composition as a function of conversion. Skeist's work is based on the analogy between the variation of polymer composition as a function of conversion and the Rayleigh equation which describes the composition of a binary distillation as a function of fraction distilled. Jean Guillot (Makromol. Chem., Macromol. Symp., 35/36, 269-289 (1990)) uses a different approach, applying reactivity ratios and empirically-fit kinetic equations to estimate copolymer bulk compositions.

According to the present invention a method is obtained for estimating the composition of the polymer as a function of conversion, then the calculation of numerous physical properties, which depend on the polymer composition, can be readily performed. Step (a) of the instant inventive process enables determination of polymer compositions (monomer sequence distribution) of polymers containing from two to thirty different monomers or monomer types, using chemical reaction kinetics theory and experimentally measured monomer reactivities.

Figure 27:
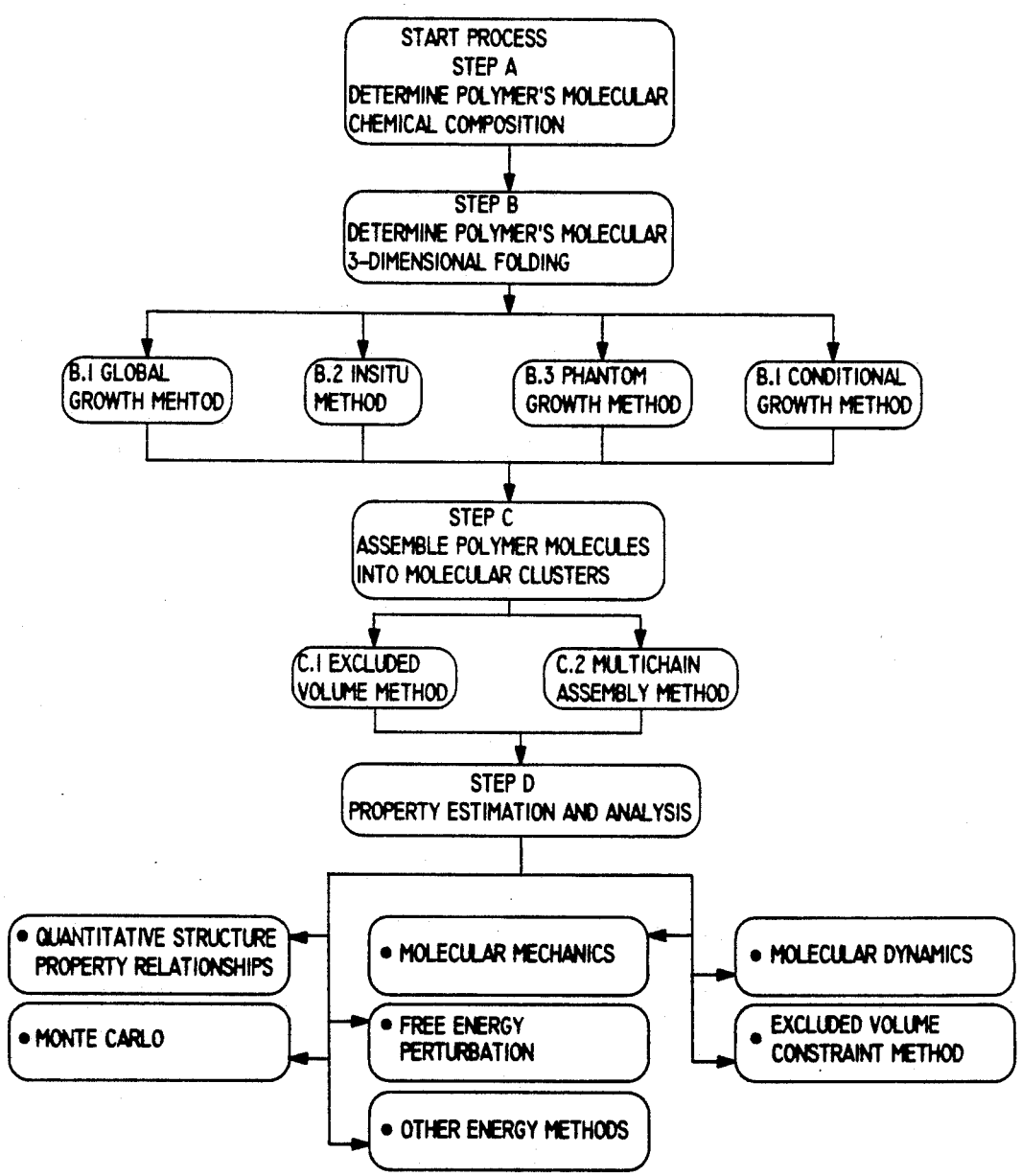
FIG. 27. is a schematic diagram showing the relationship between the different process steps embodied and broadly described by the present invention.

FIG. 27 is a block diagram of the overall system of the present invention identifying in the blocks 10 to 26 the respective operation in the steps of the process outlines above. FIG. 27 in block 10 represents the step (a) of determining the proposed polymeric substance of molecular chemical compositions through estimation of individual polymer chain chemical composition. Blocks 11-15 represent step 9b) in determining the polymer's molecular 3-dimensional folding by estimating properties of the chemical composition. As this step 9b) represented by block 11 may be performed by a plurality of numerical methods block 12 represents (B1) the global growth method, block 13 represents (B2) the In Situ Growth Method, block 14 represents (B3) the Phantom Growth Method and block 15 represents (B4) the Conditional Phantom Growth Method. Blocks 16 to 18 represents the step (c) of assembling the 3-dimensional folded molecular composition into a polymeric or copolymeric cluster. As this step 9c) represented by block 16 may be performed by a plurality of methods, block 17 represents (C1) the method using molecular excluded volume constraints determined by vector geometry. And block 18 represents (C2) the method of using a step (b) interactively. Blocks 19-26 represent step (D) of estimating the physical properties of the resulting polymeric or copolymeric cluster.

Figure 4:
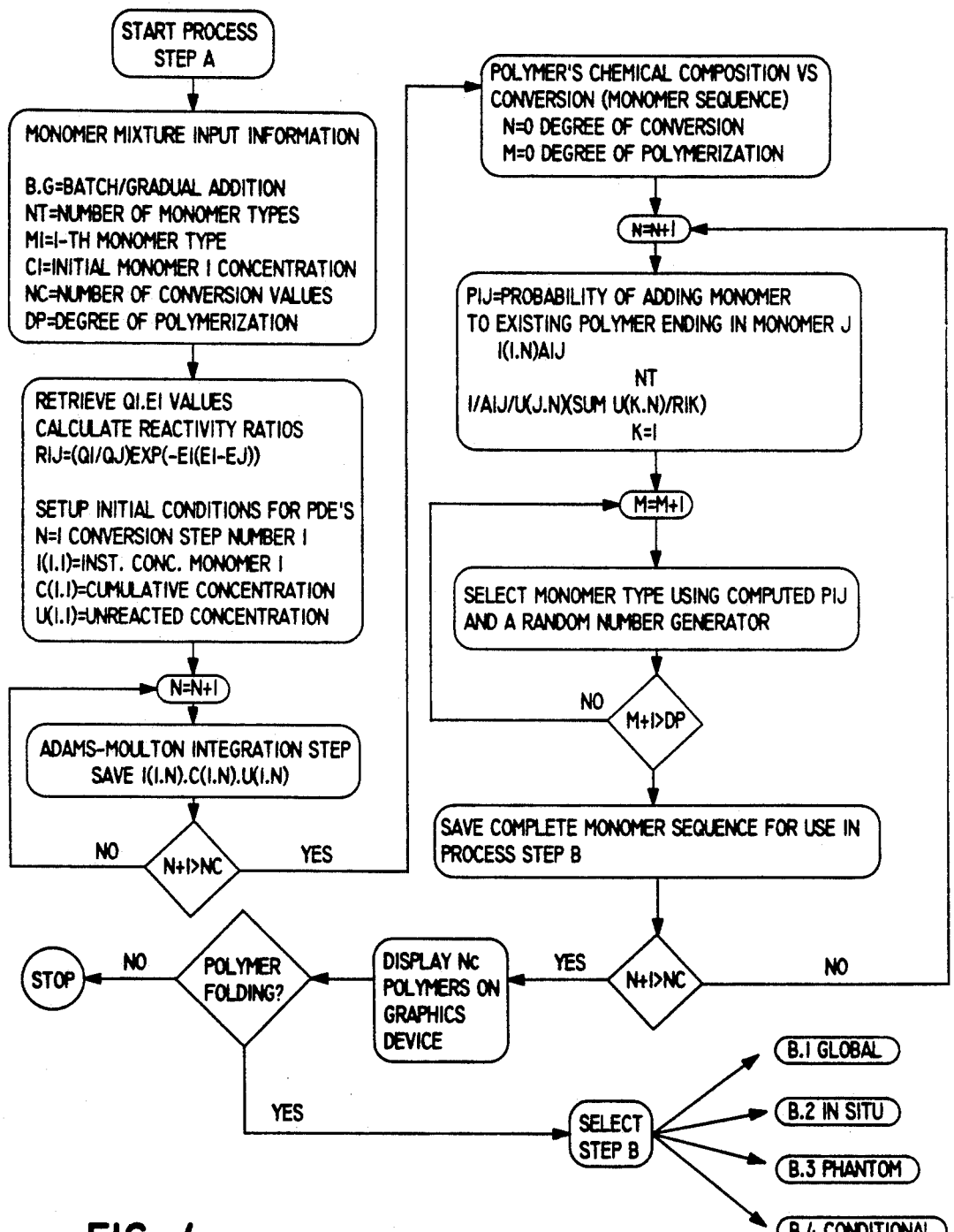
FIG. 4. is a schematic diagram illustrating the method for defining or determining the proposed polymeric or copolymeric substance or material's molecular chemical composition.

As this step D represented by block 1-9 may be performed by a plurality of methods, blocks 20 to 26 represent such methods. Block 20 represents estimation of the physical properties of the resulting clusters by quantitative property relationships. Block 21 represents the use of the standard molecular modeling technique of molecular mechanics. Block 22 represents the use of the molecular dynamics. Block 23 represents Monte Carlo methods. Block 24 free energy perturbation methods; block 25, the extended volume constraint method and block 26 represents other available energy methods. FIG. 4 is a schematic diagram for the steps of defining or determining the proposed polymeric of copolymeric substance or material's molecular chemical composition.

The logic flow chart of FIG. 4 illustrates step A operation. In this step from the mix of potential monomers there is a selection of information on a sequence of monomers to form a desired monomer. Block 27 represents the start of the determination process. Block 28 represents the input information on the monomer mixture.

Thus rectangle 28 represents reading in of the monomer types, the conditions and kind of polymerization which determine the selection of the monomer for processing. Rectangle 29 represents the computation of the reactivity ratios for this polymerization. The oval 50 represents the addition of the next monomer, or the count for the next step. Rectangle 51 represents the integration of chemical equation by the Adams- Moulton step, the output of which goes to the decision step 52 to determine whether the monomer conversion has reached the desired polymer. If not, the procedure loops back to oval 50 and repeats the integration step. If yes, the procedure then goes to monomer-polymer sequences to a decision point.

Rectangle 53 represents the selected monomer and the polymer's chemical composition. The oval 54 represents the conversion and rectangle 55 represents the calculations on the procedure, followed by the addition of monomer represented by the following rectangle 57 using the calculations product in selecting the monomer type. At the decision diamond 58 the question is, has the polymer grown to he desired length? If no, the procedure loops back to oval 56 to add a monomer to get the chain long enough, or to the desired degree of polymerization. If the decision is yes, the rectangle 59 represents the step of storing the complete monomer sequence for later use as for example in Process Step B.

Diamond 60 represents the decision point for the question, is the procedure OK, if no it should be repeated for a different level of conversion i.e. a different kind of polymer. If the decision is no, the procedure loops back to the addition command at oval 54, before the Adams-Moulton step. This represents doing the step A more than once for the selected polymer. Stated otherwise, the question is, in the monomer sequence is the order of the polymer chain length adequate? If yes, the rectangle 61 represents proceeding to a display of the polymer. Diamond 62 represents the decision point on the question whether to proceed to polymer folding. If yes, then proceed to Step B, rectangle 11. If not, proceed to stop point 63.

3-Dimensional Polymer Folding

As stated above, small molecules have properties dependent mostly on the equilibrium structure of just a few conformations. A polymer has a hugh number of roughly equivalent "stable" structures.

Experimentally it has been found that most polymer structures follow Gaussian statistics in their spatial distributions. An existing theory is able to explain such experimental findings, and mathematical expressions are available which reproduce the experimental results quite well. (See Flory, P. J., "Spatial Configuration of Macromolecular Chains", Nobel Lecture, Dec. 11, 1974, in "Selected Works of Paul J. Flory, Mandelken, Mark, Suter, Yoon Eds. Standford University Press, V. 1. (5), 1985.) The instant invention utilizes such theory to estimate the shape, by three-dimensional folding, of large polymer molecules. The methods for growing polymers from the monomer sequence distribution are Global Growth, In Situ Growth and Simple and Conditional Phantom Growth. Each method uses techniques similar to the molecular statistical thermodynamic theories found in Flory, P. J., "Statistical Mechanics of Chain Molecules", Wiley-Interscience, New York. (1969).

Global Growth Method

This growth method is repeated using of the previously generated sequence until entire polymeric chain growth is completed as illustrated by this loop back at decision point 44.

In order for the polymer conformation to be representative of =Blotzmann distribution of energies at temperature T, global minimization of a Molecular Mechanics force field is used to generate statistical weights for each of the possible conformations. For vinyl polymers without side chains there are 9 possible conformations at each new monomer addition

| tt | tg+ | tg− |
| g + t | g + g+ | g + g− |
| g − t | g − g+ | g − g− |

After global minimization of each of the nine structures, the energy is kept and probabilities are calculated from the minimized energies of each conformation (j=1,. . . ,9) of the polymer including the i-th monomer:

$$P_{ij} = \exp(-E_{ij}/RT)/Z_i \qquad (1)$$

where the $E_{ij}$'s depend on the conformation of the previous i-1 monomers, and $$Z_i = \sum_j P_{ij} \quad (2)$$

Figure 5:
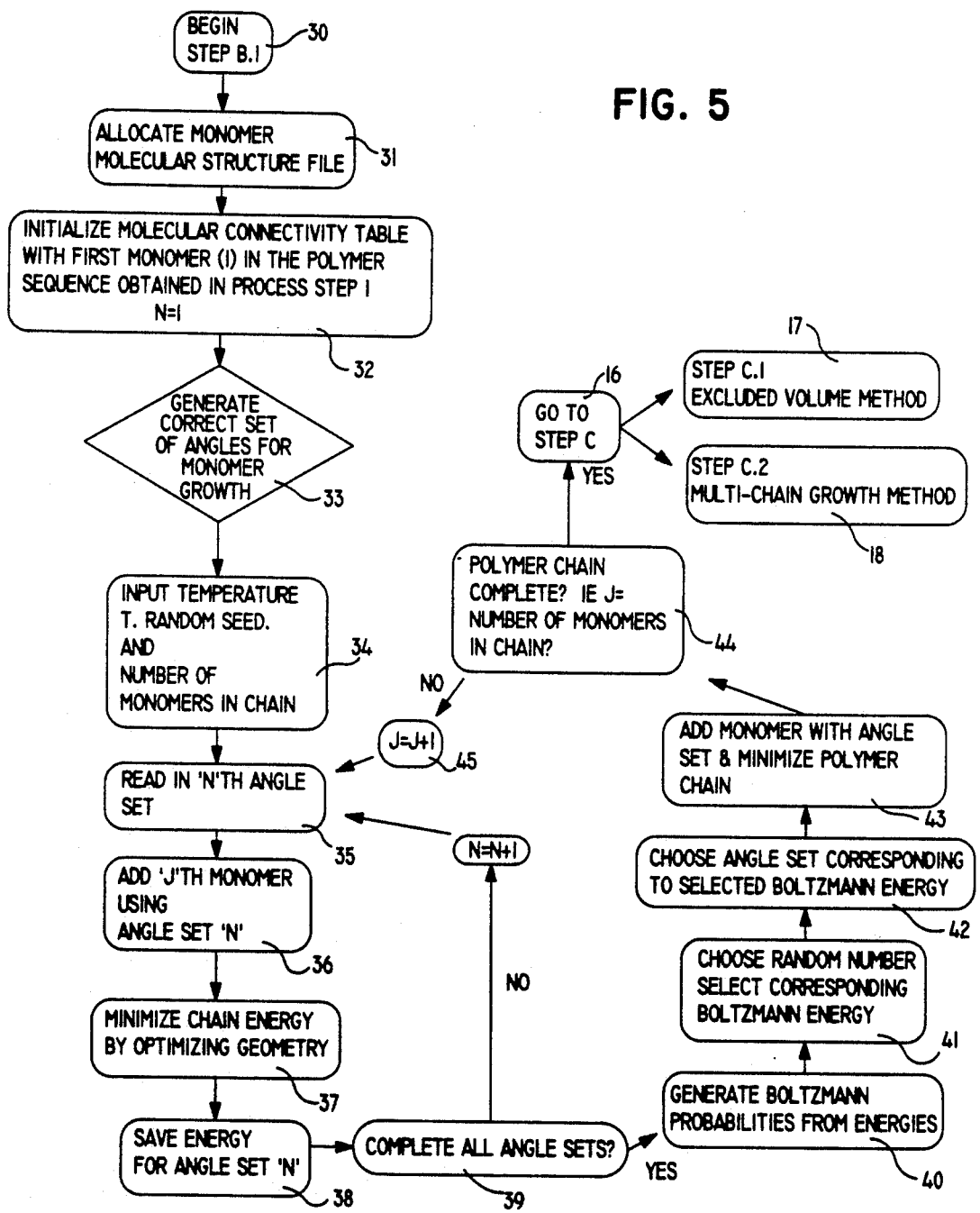
FIG. 5. is a schematic diagram illustrating the Global Growth method.

FIG. 5 illustrates the global growth outline of polymer folding. First we read in the x, y, z coordinates of the monomers in the polymer sequence. We start the 3-d polymer connectivity with the first monomer from the previously generated sequence $$Z_i = \sum_j P_{ij}$$

This growth method is repeated for each monomer of the previously generated sequence until the entire polymer chain is grown.

The logic flow chart of FIG. 5 illustrates the operation of the global Growth Method of the polymer folding. The block 30 represents the initiation of the program which is repeated for each monomer of the previously generated sequence until the entire polymer is generated. Block 31 represents allocation of the acquired x, y, z coordinates of each of the monomers of the sequence. The molecular structure file has the coordinates in it from data previously acquired and represents how the sequence is put together. This precedes data processing. Rectangle 32 represents initializing the data processing by initializing the molecular connectivity table and a selection of angles. The angles are represented by the possible conformation referred to above, as for example 9 for vinyl polymers. Diamond 33 represents the decision point as to how many angles are desired. The angles are described above. The rectangles 34 to 43 represent the steps to the decision point 44 as to whether the polymer is complete. It will be understood that the program loops back at oval 39 to the angle recording step at 35, if all the conformations have not been accomplished. Rectangle 35 represents determining the angle of the next sequential conformation. Rectangle 36 represents adding the conformation. Rectangles 37 and 38 represent energy minimization. Rectangles 40, 41, 42 and 43 represent the determination of Boltzman distribution of the polymer conformation to provide the polymer chain.

At the decision point 44 the question is, is the polymer chain complete? If the answer is not, the procedure loops back thru the instruction in the oval 45 to add.

Figure 9:
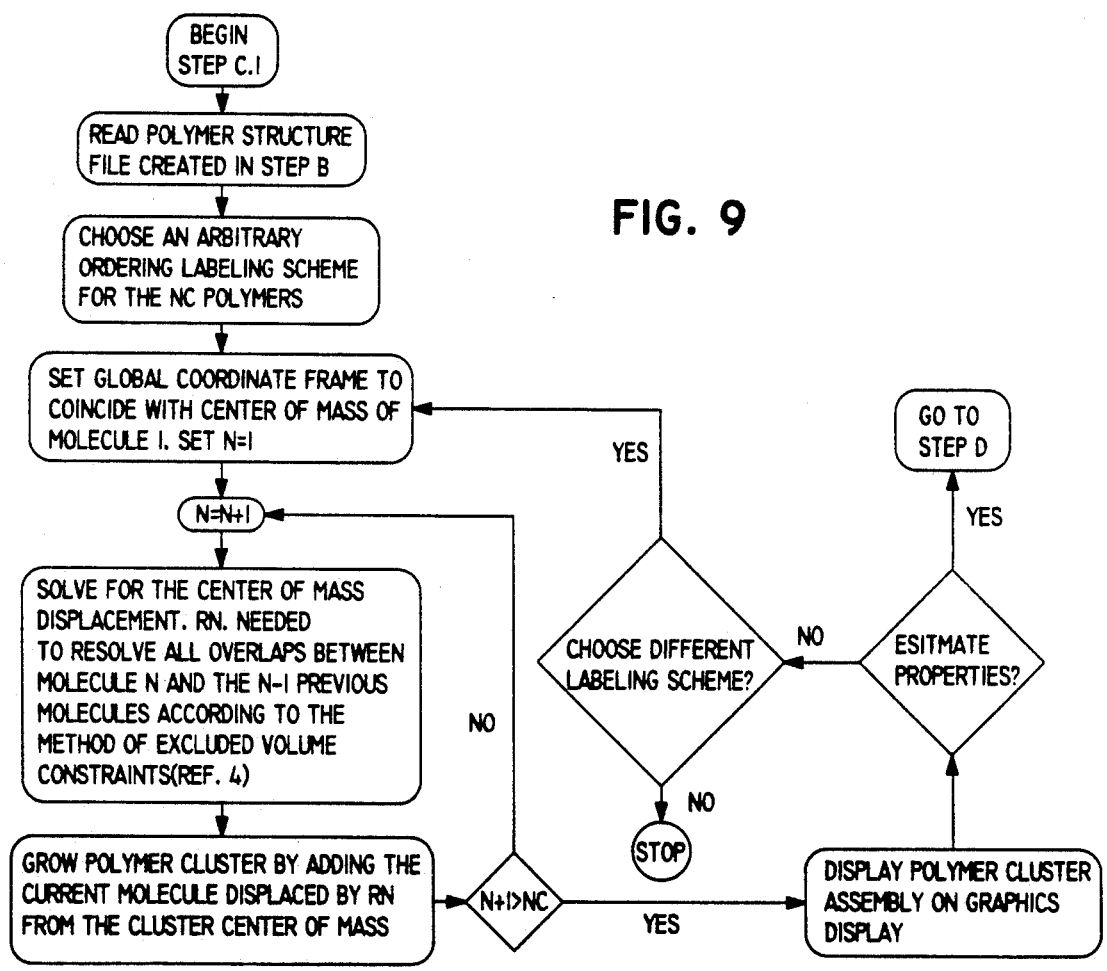
FIG. 9. is a schematic diagram illustrating the polymer assembly step using vector geometry.
Figure 10:
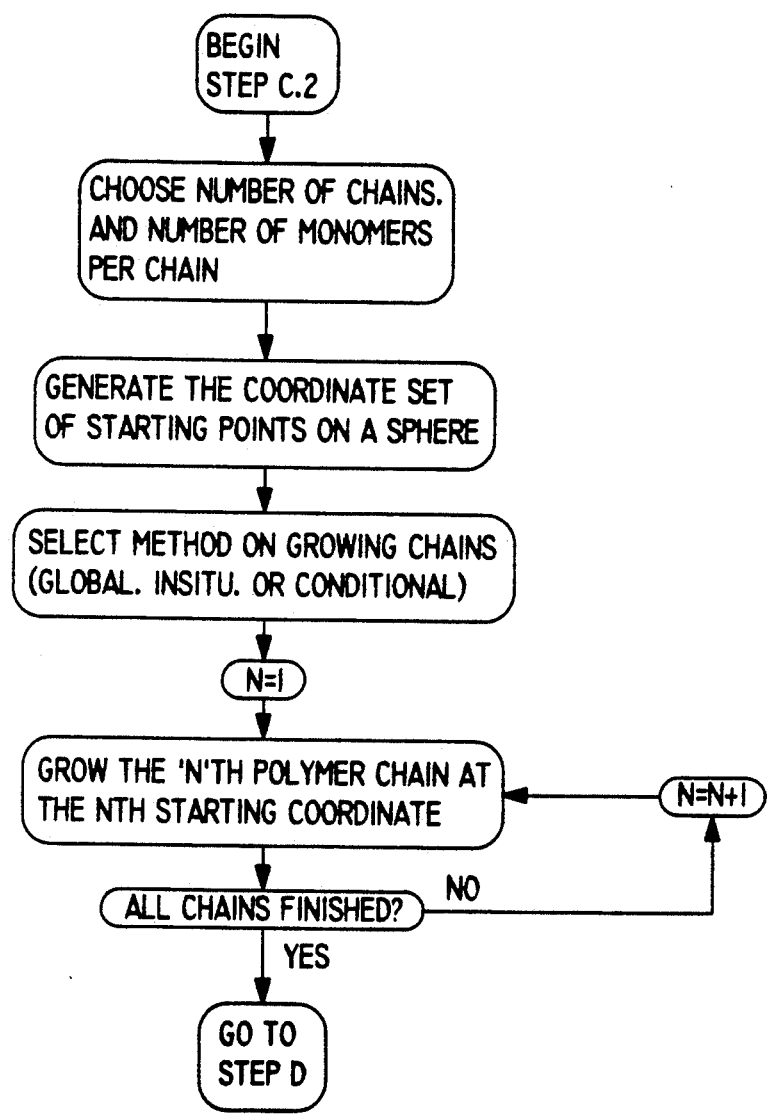
FIG. 10. is a schematic diagram illustrating the multichain growth method for simulating glassy polymer growth.

If the answer is in the affirmative and the entire sequence is grown, the procedure goes to step C which is the cluster step illustrated in FIG. 27, 9 and 10. Step C is provided for occasions when a cluster step is needed.

In theory this would provide the best answer to the determination of a Boltzmann distribution of polymer conformations at a given temperature T. In practice, however, global minimization is too slow for the size of polymers (i>10) of interest. The calculation of minimized energy grows at the rate of the square of the number of atoms in the chain (N**2). Therefore, approximations imply a reduction of the range and type of correlations between atoms along the polymer backbone. Others simplify the force field to speed up the calculations.

In Situ Growth Method

One method to mimic global optimization is by In Situ Growth. The In Situ method considers only the few monomers which are at the growing end of a chain i.e. the movable monomers. The method selects the number of monomers to use, usually 3, and a distance shell around these monomers to include in the surrounding atomic environment in the calculations. Then a new monomer is added in all its possible conformations (i.e. for a vinyl monomer, 9 sets of angles, for a chiral vinyl monomer, 18 sets of angles), each choice of monomer addition and set of angles describing each conformation is minimized with the force field, including only atoms in the chosen environment. The minimized energies are computed, and a probability vector is generated, with one value for each locally stable structure. These probabilities are temperature dependent. Probabilities are calculated from the minimized energies of each conformation (j=1,...,N) of the polymer including the i-th monomer following the equation $P_{ij}=\exp(-E_{ij}/RT)/Z_i$.

Figure 6:
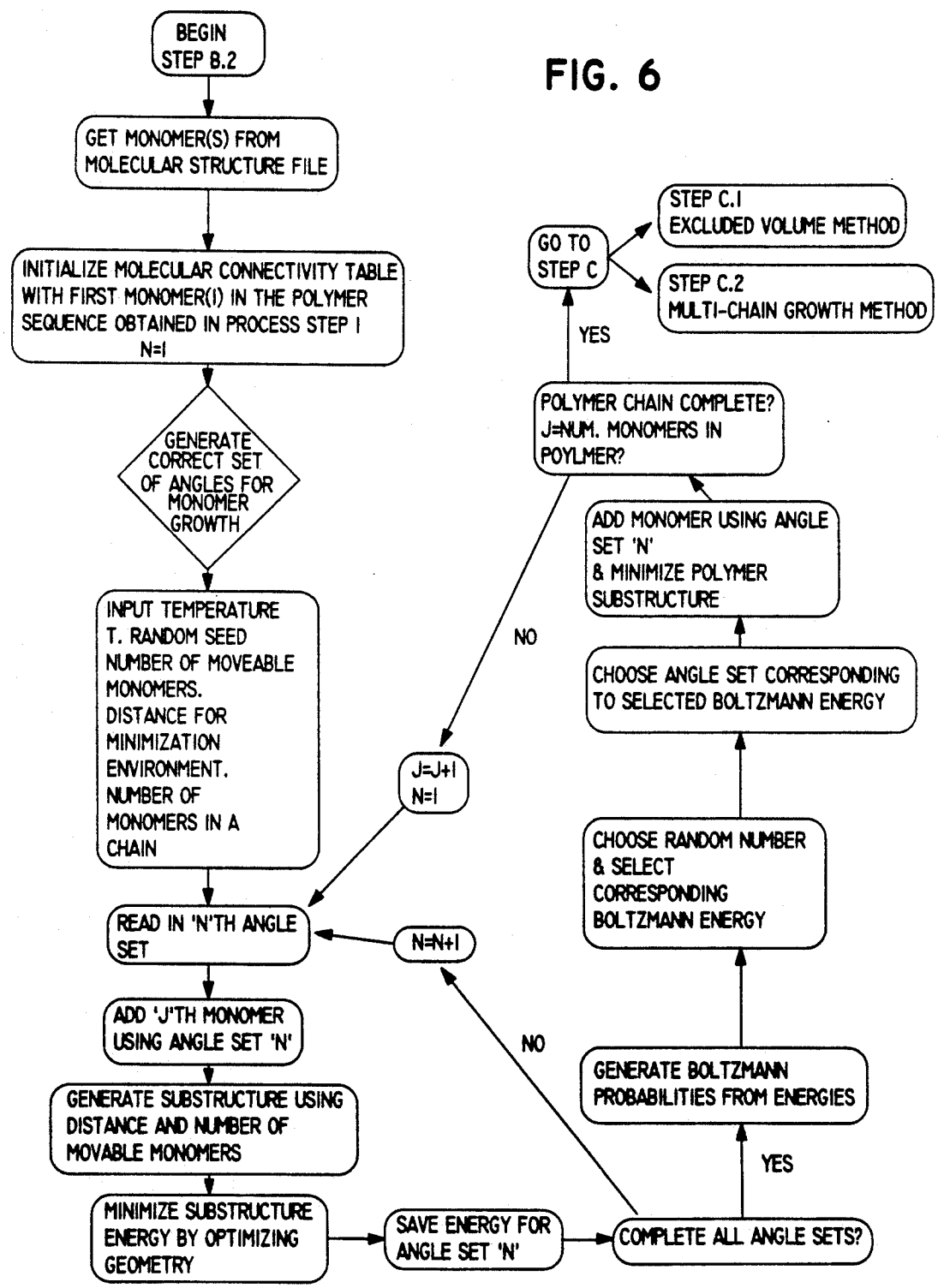
FIG. 6. is a schematic diagram illustrating the In Situ Growth method.

A random number is generated form a uniform [0,1] distribution and the structure whose probability interval contains that random number is chosen. Then the method is repeated. The set of growing monomers slides down the chain by one monomer unit, and a new distance environment atom set is selected. All possible conformations are computed for adding a new monomer, and the probability vector regenerated from the energies. This approach can be used to predict solvation effects by including a representable, yet small, number of solvent molecules within the "sphere" of the growing polymer end. One way in which this method has been implemented is by the use of MacroModel's© substructure optimization, i.e., energy minimization is constrained to a sphere (usually a distance equal to 2-10 Å) around the last monomer added to the chain. The rest of the chain remains fixed although a few atoms are still allowed to move slightly while being constrained by parabolic force constants. FIG. 6 is a flow chart diagram illustrating the In Situ Growth method.

The logic flow chart of FIG. 6 illustrates the operation of the In Situ Growth Method of polymer folding. The program is initiated by the reading out of the monomer from the Molecular Structure file. The rectangle 64 represents allocation of the x, y, z coordinates of each monomer. Rectangle 65 represents initializing the date processing of the molecular Connectivity Table and selection of angles. The diamond 66 represents selection of the monomers and the angles. The angles are described above. The rectangles 67 to 80 represent steps to the decision as to whether the polymer is complete. It will be understood that the program loops back at oval 74 to the angle read-in step at 68, if further conformations are to be added. Rectangle 68 represents determining the angle and rectangle 69 represents adding the monomer in all possible conformations. Rectangle 71 represents the minimization of each conformation. Minimization refers to energy minimization as known in rectangle 73 represents the decision point as to whether all the angle sets for the monomer have been completed. The negative branch from the decision at 73 carries the program back to reading in another angle set about adding the monomer. The affirmative branch carries the monomer to the step represented by rectangle 75 and the Boltzman determination wherein the probabilities are calculated from the minimized energies of each conformation of the polymer. Rectangle 76 represents the choosing of a random number described above, the selection a structure is represented in rectangle 77. In the next step, represented by rectangle 78 the set of growing monomers take place and at the decision point of rectangle 80 the decision question is, is the polymer chain complete? The negative branch carries the program back to the step of the reading in another angle set at rectangle 68 toward completing the polymer. The affirmative branch carries the procedure to step C.

Simple Phantom Growth Method

The Simple Phantom Growth method reduces J. P. Flory's theory to a Simple Markov process, wherein conformational probabilities depend only on the conformation of the previously added monomer. As such, nine probabilities of adding a monomer are calculated from energies of adding a single monomer to another. Long range effects are neglected.

Implementation includes intradyad and interdyad probabilities. As an example consider the following polymer conformation sequence:

| (1) Polymer Conformation | t | g+ | g+ | t | t | t | g− | g− | g+ | t | t | g+ |
|---|---|---|---|---|---|---|---|---|---|---|---|---|
| (2) Intradyad Conformations | | (tg+) | (g + t) | | (tt) | | (g − g−) | | (g + t) | | (tg+) | |
| (3) Interdyad Conformations | | | (g + g+) | (tt) | | (tg−) | | (g − g+) | | (tt) | | |

Figure 7:
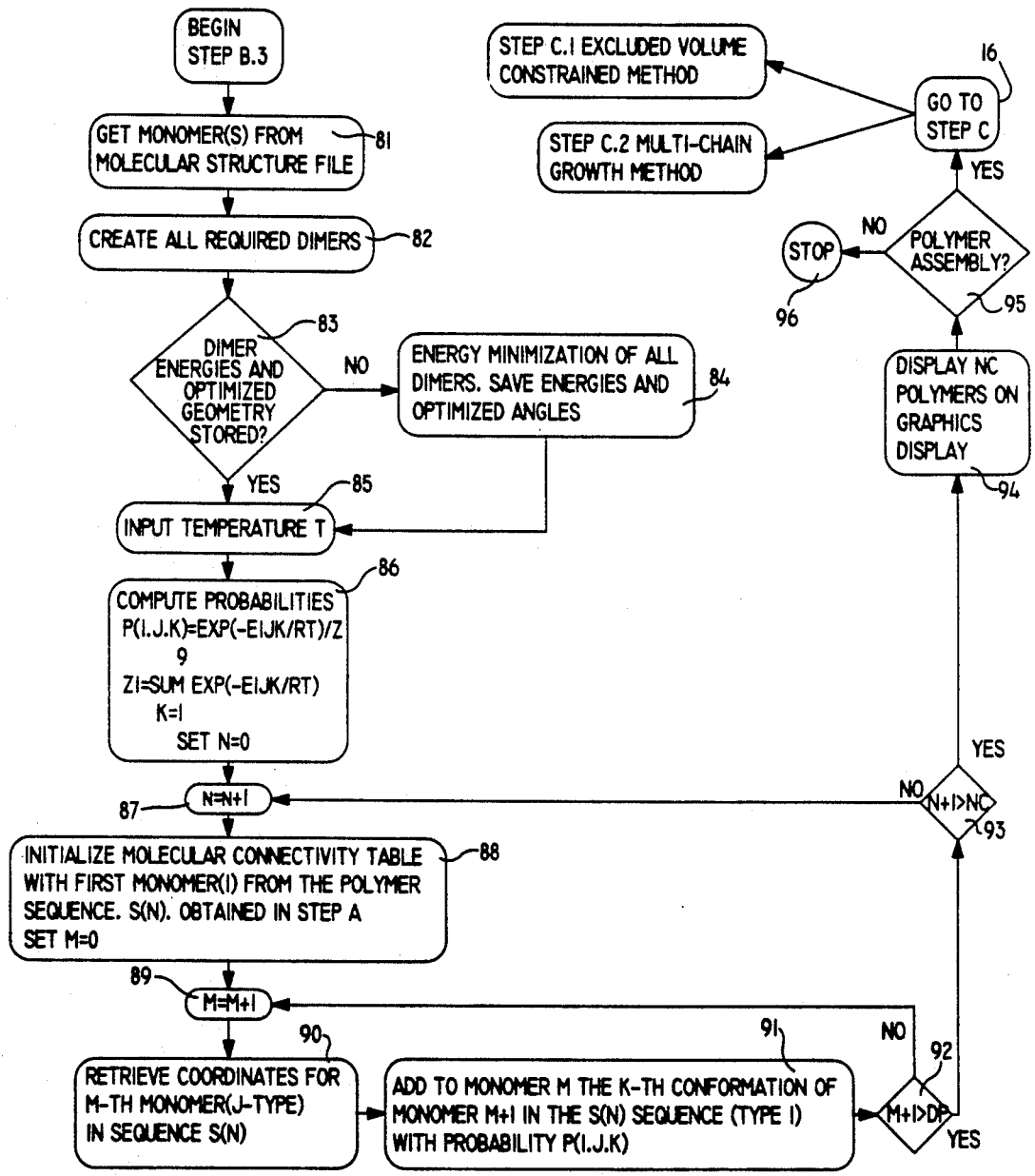
FIG. 7. is a schematic diagram illustrating the Simple Phantom Growth method.

Although this method is the fastest way to model the folding of polymer molecules, the shortness of range of correlations in neighboring polymer conformations result in highly coiled, and self-crossing (quite often one self-crossing every four monomers) chains. Consequently the energy distribution is highly non-Boltzmann. FIG. 7 is a block diagram illustrating the Simple Phantom Growth method. Use of the Conditional Phantom Growth method greatly alleviates the non-Boltzmann distribution.

The logic flow chart of FIG. 7 illustrates the operation of the Phantom Growth Method of polymer folding. The block 14 represents the initiation of the program. Rectangle 81 represents reading the monomer structures form a file. Rectangle 82 represents creating all possible dimers. For a sample vinyl polymer with no side chains, this is nine dimers. Rectangle 84 represents minimize the dimers and saving the optimized energies ($\Sigma_{ij}$) in a table. Diamond 83 represents the question are the dimers energies optimized as read in from rectangle 82. The negative branch carries the program to rectangle 84 and the affirmative branch to rectangle 85 representing an input temperature. Rectangle 86 represents computing the probabilities by using Boltzman probabilities for the ith $\Phi$ and the jth $\Psi$ and the kth monomer as shown in the equation $$P_{ijk} = \frac{\exp(-\epsilon_{ij}/RT)}{\sum_{k=1}^{9} \exp(-\epsilon_{ij}/RT)}$$

Oval 87 represents the monomer number and rectangle 88 represents setting up the monomer connectivity table. The monomer is from an earlier sequence.

Oval 89 represents adding a monomer with a particular $\Phi$ and $\Psi$ value. Rectangle 90 represents retrieving coordinates of the mth monomer and selection of a uniform random number. Rectangle 91 represents the value of the random number is compared to the $\Phi$, $\Psi$ probability intervals in the table. It is noted that the interval that corresponds to the chosen random number determines the $\Phi$, $\Psi$ value for the monomer addition. Diamond 92 represents checking to determine whether the chain is complete, i.e. the degree of polymerization has been reached. The negative branch carries the program back to oval 89 to add another monomer.

The cycle is repeated until the required different chains have been generated. The diamond 93 represents checking on completion of the desired polymers. Rectangle 94 represents proceeding to display of the polymer. Diamond 95 represents the decision point on the question whether to proceed to polymer assembly. If yes, then proceed to Step C, rectangle 16. If no, proceed to stop point 96.

Conditional Phantom Growth Method

In the Conditional Phantom Growth method, longer correlations are built by computing conformational probabilities from optimized trimers which include up to five bond correlations. Optimized "trimer" energies are used to calculated row vectors of conditional probabilities as follows:

Example:

| Monomer i-1 ↓ | Monomer i → | | | | | | | | |
|---|---|---|---|---|---|---|---|---|---|
| | g + g+ | g + g− | g + t | g − g+ | g − g− | g − t | t g+ | t g− | t t |
| g + g+ | 0.701 | 0.032 | 0.000 | 0.004 | 0.000 | 0.000 | 0.245 | 0.016 | 0.002 |
| g + g− | 0.000 | 0.000 | 0.000 | 0.829 | 0.084 | 0.036 | 0.049 | 0.002 | 0.000 |
| g + t  | 0.233 | 0.001 | 0.000 | 0.625 | 0.020 | 0.016 | 0.099 | 0.005 | 0.001 |
| g − g+ | 0.818 | 0.012 | 0.000 | 0.000 | 0.000 | 0.000 | 0.155 | 0.008 | 0.006 |
| g − g− | 0.000 | 0.000 | 0.000 | 0.854 | 0.051 | 0.030 | 0.061 | 0.004 | 0.000 |
| g − t  | 0.267 | 0.004 | 0.001 | 0.215 | 0.013 | 0.009 | 0.469 | 0.017 | 0.004 |
| t g+   | 0.631 | 0.182 | 0.000 | 0.000 | 0.000 | 0.000 | 0.170 | 0.016 | 0.001 |
| t g−   | 0.000 | 0.000 | 0.000 | 0.295 | 0.032 | 0.027 | 0.621 | 0.023 | 0.003 |
| t t    | 0.162 | 0.002 | 0.000 | 0.550 | 0.026 | 0.029 | 0.223 | 0.008 | 0.000 |

Once a conformation is selected for the Current monomer, a van der Waals distance check is conducted. If large van der Waals repulsions are found then one monomer is backtracked and a different conformation is chosen (in the average the second most probable conformation will be chosen). If no conformation can be found to overcome van der Waals repulsion, the In Situ Growth method is used for optimization of the current monomer addition.

Figure 8:
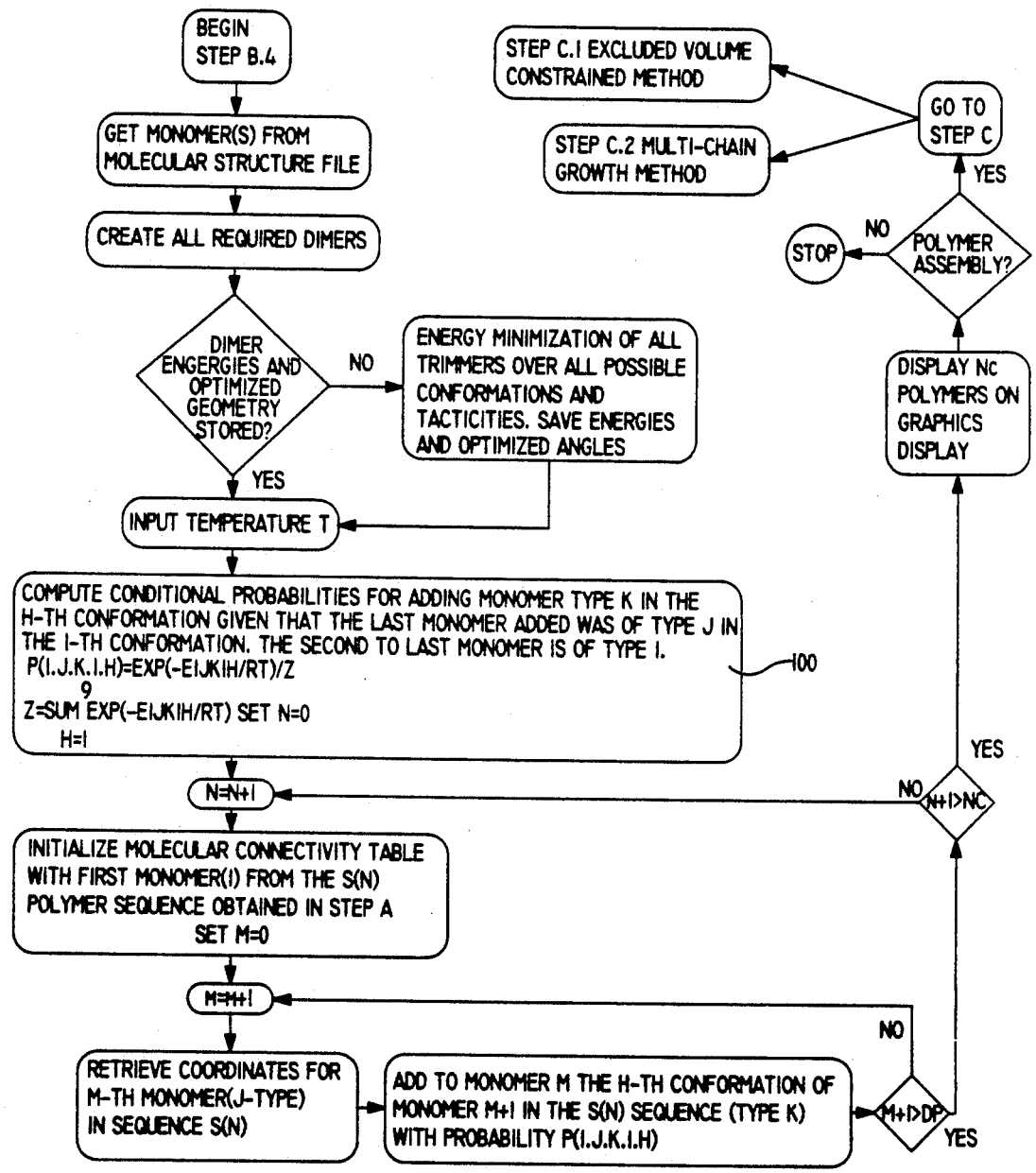
FIG. 8. is a schematic diagram illustrating the Conditional Phantom Growth method.

Conditional Phantom Growth provides to the average probability weights which are good approximations to the average values obtained in the In Situ method. The folding of polymer molecules is quite efficient, hundreds of folded polymers can be calculated in a matter of minutes. The resulting energy distribution closely follows Boltzmann statistics, there is some long range conformation correlation and molecular energies are very often acceptable even though the initial monomer geometries used have only nominal values for t, g+, and g− angles. Quite often the molecular structures can be minimized without singularities when no self-crossing occurs. The backbone conformation preserves its general shape even after minimization and end-to-end distances vary by less than 1% after minimization. FIG. 8 is a block diagram illustrating the Conditional Phantom Growth method.

The logic flow chart of FIG. 8 illustrates the operation of the Conditional Phantom Growth method. The rectangles, diamonds and ovals of FIG. 8 represents similar steps in the flow chart of FIG. 7 which is referred to. A difference is found at rectangle 100 in FIG. 8 which represents computing conditional probabilities for adding monomer type k in the h-th conformation given that the last monomer added was of type j in the l-th conformation.

Polymer Cluster Assembly

The assembly of the resulting 3-dimensionally folded molecular composition into a proposed polymeric or copolymeric cluster is created as follows. From a statistical distribution of individual molecules, a polymer cluster reminiscent of the polymer in the bulk is fabricated. Then the model builder selects one of two methods; one method uses new excluded volume constraints derived from analytical vector geometry and the individual polymer structures of step (b). See figure (9), from "Molecular Silverware: General Solutions to Excluded Volume Constrained Problems", by Mario Blanco, Journal of Computational Chemistry, accepted for publication Jul. 3, 1990.

For the purpose of resolving molecular overlaps each molecule is modeled as a rigid body, i.e., as a collection of hard spheres. The size of each sphere is set by the van der Waals radius of the corresponding atom. Of course, covalently bound atoms necessarily have overlapping van der Walls spheres. We are only concerned with the resolution of van der Walls overlaps between non-bonded atoms.

Two rigid bodies require six degrees of freedom to have their relative orientations and positions in free space completely specified. We choose the first three degrees of freedom to be the euler angles, $\Omega = (\alpha, \beta, \gamma)$, which define the orientation of molecular 2 in a coordinate frame affixed to molecule 1. The vector connecting the centers of mass of both molecules, in polar coordinates $(r, \theta, \phi)$, completes the list of six, initially independent degrees of freedom. One of these r, becomes a function of the other five when the excluded volume constraint equations are enforced. We seek the form and the solution of these equations.

Figure 1:
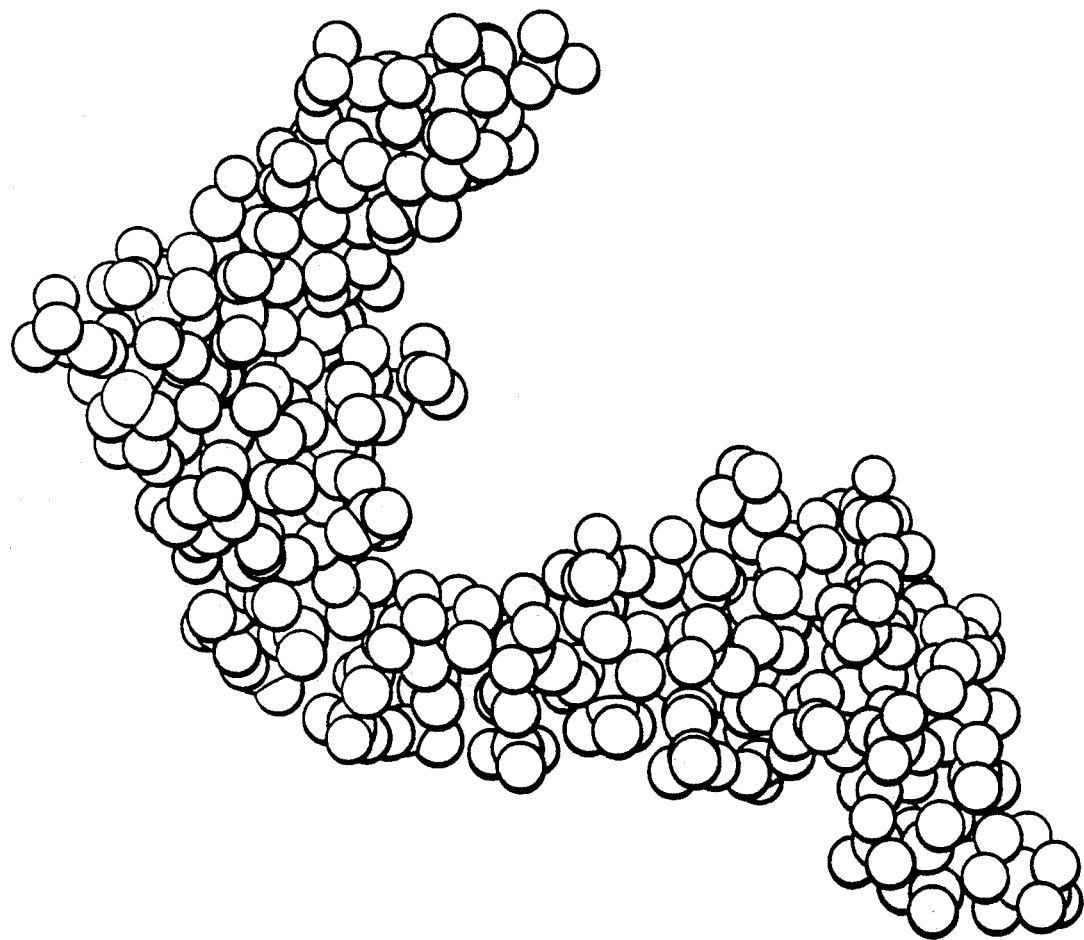
FIG. 1. is a computer generated picture of a three-dimensionally folded model of atactic polymethylmethacrylate.

The global coordinate reference frame is depicted in Annex FIG. 1. The frame is affixed to the center of mass and oriented along the principal moments of inertia axes of molecule 1. The atoms are number $i=1,2,\ldots,N_1$. Atoms in molecule 2 are numbered $j=N_1+1, N_1+2, \ldots, N_1+N_2$. In the final self-avoiding assembly the vector location of all atoms in molecule 2 will be given by two rigid body operations, a rotation $R_\Omega(\alpha, \beta, \gamma)$ and a translation r n, applied to the original atomic position vectors $r_j^o$ $$r_j = R_\Omega(\alpha, \beta, \gamma) r_j^o + r\, n;$$

$$j = N_1+1, N_1+2, \ldots, N_1+N_2 \tag{1}$$

n is a unit vector in the polar direction $(\theta, \phi)$, $$n = (\sin\theta \cos\phi, \sin\theta \sin\phi, \cos\theta) \tag{2}$$

$R_\Omega(\alpha, \beta, \gamma)$ is a $3 \times 3$ direction cosine matrix[4]

$$R_\Omega(\alpha, \beta, \gamma) = \begin{bmatrix} \cos\gamma \cos\beta \cos\alpha - \sin\gamma \sin\alpha \\ -\sin\gamma \cos\beta \cos\alpha - \sin\gamma \sin\alpha \\ \sin\beta \cos\alpha \end{bmatrix}$$

The original orientation of molecular 2, $\Omega_o = (\alpha=0, \beta=0, \gamma=0)$ is taken to be the orientation which aligns its principal axes with the principal axes of molecule 1. Before the rigid body operations are applied, the centers of mass of both molecules coincide at the origin of the global coordinate reference frame. We now discuss the excluded volume constraint equations and the solutions for several cases in increasing order of complexity.

$$M = 2, N_2 = 1$$

Figure 2:
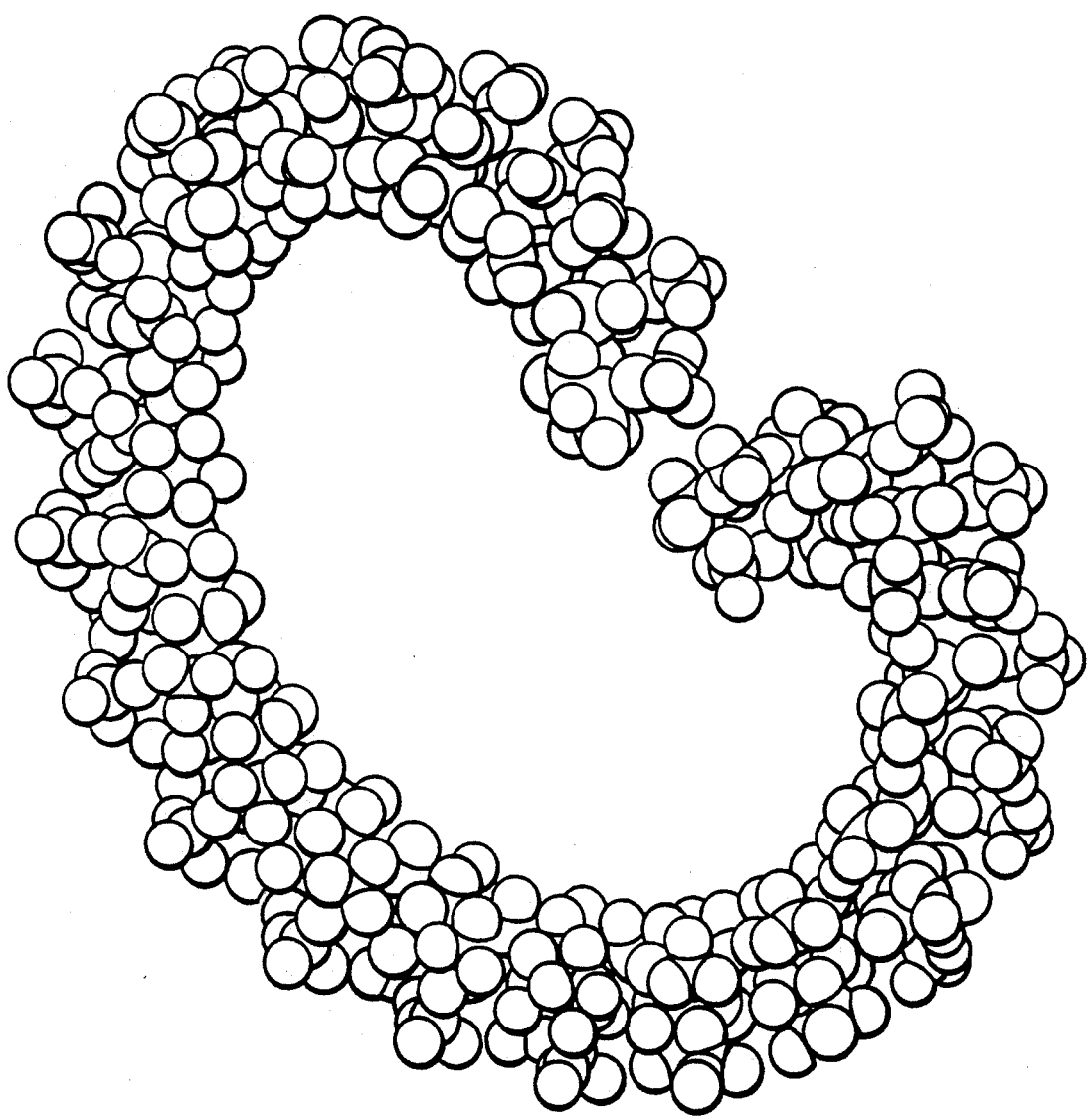
FIG. 2. is a computer generated picture of a three-dimensionally folded model of syndiotactic polymethylmethacrylate.

The excluded volume constraint equations can be written in the following general form $$\phi_{ij}(r, \theta, \phi) \geq 0$$

$$i = 1, 2, \ldots N_1, j = N_1 + 1 \tag{4}$$

where $$\Phi_{ij}(r, \theta, \phi) = r^2 + 2\left(r_+ \cdot \frac{n}{ij}\right)r + |r_{ij}|^2 - (s_i + s_j)^2 \tag{5}$$

and $r_{ij}$ is the vector difference (refer to annex FIG. 2).

$$r_{ij} = r_j - r_i \tag{6}$$

$s_i$ and $s_j$ are the van der Walls radii of the corresponding atoms. Because in the first case "molecule" 2 is monoatomic the Euler angles $\alpha$, $\beta$, and $\gamma$ are all set to zero and the rotation matrix becomes a $3 \times 3$ unit matrix.

Annex FIG. 2 depicts how the excluded volume constraint expression (5) was obtained. An equation for the magnitude r of the translation vector along the n line of sight was derived from the expression for the magnitude of the vector addition $$|r_{in} + r\, n|^2 = (s_i + s_j)^2 \tag{7}$$

Expansion of the left hand side leads to expression (5). The solution and a physical interpretation of expression (5) follows.

The displacement needed to place the atom j in contact with atom i along a line of sight given by the direction n is obtained by setting $\Phi_{ij}$ to the minimum value allowed by the constraint eq. (4), i.e., $\Phi_{ij}(r, \theta, \phi) = 0$. Solving for r one gets $$r^{\pm}_{ij} = (r_{ij} \cdot n) \pm [(r_{ij} \cdot n)^2 - |r_{ij}|^2 + (s_i + s_j)^2]^{\frac{1}{2}} \qquad (8)$$

$r_{ij}^-$ places atom j on the near side of atom i while $r_{ij}^+$ places it on the far side. Negative values of $_{ij}r_-$ or $r_{ij}^+$ are interpreted as positive displacements along the $-n$ direction. Notice that two complex roots result if $$(r_{ij} \cdot n)^2 - |r_{ij}|^2 + (s_i = s_j)^2 < 0 \qquad (9)$$

$$\begin{bmatrix} \cos\gamma\cos\beta\sin\alpha + \sin\gamma\cos\alpha & -\cos\gamma\sin\beta \\ -\sin\gamma\cos\beta\sin\alpha + \cos\gamma\cos\alpha & \sin\gamma\sin\beta \\ \sin\beta\sin\alpha & \cos\beta \end{bmatrix}$$

Figure 3:
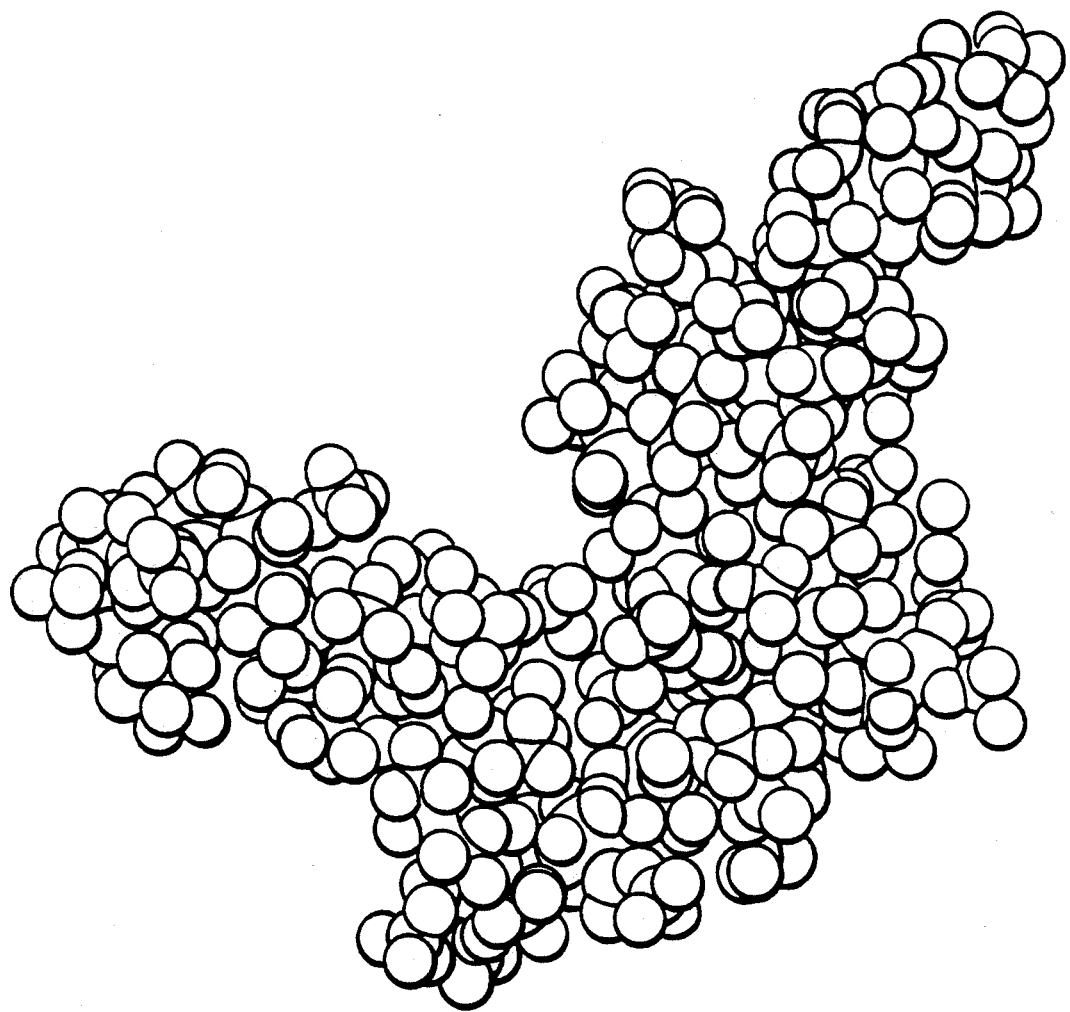
FIG. 3. a computer generated picture of a three-dimensionally folded model of isotactic polymethylmethacrylate.

Complex roots indicate that no van der Walls overlap exists along the line of sight n and thus no real displacement can put atom i and j in contact with each other. Annex FIG. 3 depicts all six possible root combinations in terms of the initial positions of atoms i and j and the n line of sight.

A more useful interpretation of eq. (4) follows. The rear roots of $\Phi_{ij}(r, 0, \phi)$ define a set of open segments on the real axis $$\lambda_{qj} = (r^{-1}{}_{qj}, r^+{}_{qj}) \quad q = 1, 2, \ldots, p \qquad (10)$$

where the index q runs only over the p real roots of $\Phi_{ij}(r, 0, \phi)$. If atom j gets translated through a vector $\Phi n$, with $\Phi$ a number contained within any $\lambda_{qj}$ segment, $$(r_{qj}^- < \Phi < r_{qj}^+ \text{ for some } q),$$

it violates constraint eq. (4). The union of all $\lambda^{qj}$ open segments constitutes the complete set of "forbidden" displacements. Conversely, the complement of the union defines all points along the line of sign n where atom j can be translated and be free from van der Walls overlaps with molecule 1. Therefore, the solution to the excluded volume constraint eq. (4) is the set $$\lambda_j^c(n) = \{\lambda_{ij} \cup \lambda_{ij} \cup \ldots \cup \lambda_{pj}\}^c \qquad (11)$$

FIG. 4 illustrates the effect of the union operation on the possible placement locations for atom j when all van der Waals overlaps are resolved. Note that because the $\lambda_{qj}$'s are open segments, their ends, the real roots of $\Phi_{ij}(r, 0, \phi)$, may be part of the set $\lambda_j^c$. However, the union operation eliminates most of the roots from the solution set. It is relatively simple to write computer code to determine which roots survive the union operation. Two roots which are never eliminated are $$r_j^- = \text{Min}_q \{r_{qj}^-\} \qquad (12a)$$

$$r_j^+ = \text{Max}_q \{r_{qj}^+\} \quad q = 1, 2, \ldots, p \qquad (12b)$$

These two immortal roots are always elements of the solution set $\lambda_j^c$ because there are no segments to the right and to the left of the right-most and left-most segments respectively. All displacement values in the ranges $$-x \leq r \leq r_j^- : r_j^+ \leq r \leq x \qquad (12c)$$

are also elements of the solution set $\lambda_j^c$. Incidentally if one leaves all values greater than $r_j^+$ and less than $r_j^-$ out of the solution set $\lambda_j^c$ one obtains an operational definition of the "probe" accessible surface. If the van der Waals radius $s_j$ is set equal to zero one get an operational definition of the multiple valued van der Walls surface of molecule 1 in polar coordinates.

$$M = 2N_1 > 1, N_2 > 1$$

The Euler angles are required in this case. There are $N_1 \times N_2$ constraint equations similar to (4)

$$\Phi_{ij}(\alpha, \beta, \gamma, r, 0, \phi) = \qquad (13)$$
$$r^2 + 2(r_{ij}^\Omega \cdot n)r + |r_{ij}^\Omega|^2 - (s_i + s_j)^2$$

where $$r_{ij}^\Omega = R_\Omega(\alpha, \beta, \gamma) r_j^0 - r_i^0 \quad i = 1, 2, \ldots, N_1; \qquad (14)$$
$$j = N_1 + 1, N_1 + 2, \ldots, N_1 + N_2$$

all other quantities have their previous meanings. The general solution to the excluded volume constraint problem is $$\lambda^c(\Omega, n) = \{\lambda_1 \cup \lambda_2 \cup \ldots \cup \lambda_{N_2}\}^c \qquad (15)$$

where $$\lambda_j = \{\lambda_{ij} \cup \lambda_{2j} \cup \ldots \cup \lambda_{N_1 j}\} \qquad (16)$$

and $$\lambda_{ij} = (r^{\Omega-}{}_{ij}, r^{\Omega+}{}_{ij}) \qquad (17)$$

For simplicity of notation all roots of eq. (13) were made to appear in the definition of solution (15) but it must be kept in mind that only the real roots are to be included. Just as before we have $$r_{ij}^{\Omega\pm} = -(r_{ij}^\Omega \cdot n) \pm [(r_{ij}^\Omega \cdot n)^2 - |r_{ij}^\Omega|^2 + (s_i + s_j)^2]^{\frac{1}{2}} \qquad (18)$$

Expression (15) makes no assumptions regarding molecular shape. All valid excluded volume constraint solutions can be found in the $\lambda^c$ set. All physically allowed self-avoiding assemblies can be created regardless of the complexity in the topologies of molecules 1 and 2 by changing the values of $(\alpha, \beta, \gamma)$ and $0, \phi)$ and solving for the $\lambda^c$ set following eqs. (16)–(18).

The operational simplicity of solution (15), its generality with respect to molecular topology, and the ability to select appropriate paths through $(\alpha, \beta, \gamma)$ and $(0, \phi)$ space are important elements for the search and development of more general molecular modeling algorithms appropriate to condensed phase simulations. From such a molecular modeling point of view an important element of the solution set is the value $r^3$ defined such that $$|r^c| = Min|\lambda^3| \qquad (19)$$

The vertical bars indicate absolute values. $r^c$ is the shortest possible displacement required by molecule 2 to resolve all atomic overlaps with molecule 1.

$M > 2$

The excluded volume constraint problem can be stated in the most general possible way as follows.

Given M molecules with fixed orientations and center of mass directions $$\Omega_m = (\alpha_m, \beta_m, \gamma_m) \qquad (20a)$$

and $$n_m = (\sin p_m \cos \phi_m, \sin 0_m \sin \phi_m, \cos 0_m) \qquad (20b)$$

respectively, find the complete set of all molecular displacements ($r_m$'s) which satisfy the excluded volume constraint equations:

$$|R_m{}^\Omega r_j{}^o + r_m n_m - R_{m'}^\Omega r_i{}^o - r_{m'} n_{m'}|^2 \geq (s_i + s_j) \qquad (20c)$$

$$\forall i < j = 1, 2, \ldots, \sum_m N_m; m > m' = 1, 2, \ldots M$$

where $r_i{}^o$ and $r_j{}^o$ are the original position vectors for atom i and atom j respectively. m' and m identify the molecules carrying atoms i and j respectively, and $N_m(m=1,2,\ldots,M)$ gives the number of atoms in molecule m.

The elements of the solution set $\lambda^c$ are M-tuples of the form $(r_1, r_2, \ldots, r_M)$. There is an infinite number of elements in $\lambda^c$. Most of them belong inside semi-infinite segments of the form (12c). From a molecular modeling point of view, however, the important solutions satisfy eq. (19) also.

Equation (20) defines a nonholonomic constraint problem. There are no general ways of attacking nonholonomic constraint problems. According to Goldstein[5] "the most vicious cases of nonholonomic constraints must be tackled individually." A practical solution to this problem is obtain by extending the method employed in the M=2 case, i.e., the components of the M-tuples are found one at a time.

We begin by placing one of the M molecules at the origin of the global reference frame ($r_1=0$). We then selected a second molecule and apply the method of the previous section to find the solution set for the two molecule system. In accordance with eq. (19) we set $r_2$ equal to min $|\lambda^c|$. Notice that we could have selected the identity of the first and second molecules in M and M−1 different ways respectively. In general there are M−m+1 ways of choosing the $M^{th}$ molecule when the assembly already contains m−1 molecules. Consequently there is a possible total of M! different molecular assemblies. Each of these assemblies is located fully in 3-D space by giving (1) the original coordinates of the atoms in each molecule $r_i{}^o$. (2) the orientations and displacement directions, $\Omega_m$ and $n_m$ respectively, and (3) the M-tuple $(r_1, r_2, \ldots, r_M)$ of molecular centers of mass displacements.

The solution method consists of the following steps
1. Choose a labeling scheme for the M molecules $$m = 1, 2, \ldots, M.$$

2. Define the following operational indexes:

$$N_1^{(m)} = \sum_{k=1}^{m} N_k \qquad (21)$$

$$N_2^{(m)} = N_{m-1}$$

3. Set the global coordinate frame to coincide with the center of mass of molecule 1. In effect we are setting $r_1=0$. Set $m=1$.

4. Calculate the value $r_{m=1}$ according to the solution method employed in the M=2 case, i.e., $|r_{m+a}| = \text{Min}|\lambda^c|$. Equations (14) and (18) now read $$r_{ij}^\Omega = R_{\Omega m+1} r_j{}^o - r_i \qquad (22)$$

$$r_-^{\Omega+} = -(r_{ij}^\Omega \cdot n_{m+1}) \pm |(r_{ij}^\Omega \cdot n_{m+1})^2 - \qquad (23)$$

$$|r_{ij}^\Omega|^2 + (s_i + s_j)^2|^{\frac{1}{2}}$$

with
$i = 1, 2, \ldots, N_1^{(m)}; j = N_1^{(m)} + 1,$
$N_1^{nm} + 2, \ldots, N_1^{(m)} + N_2^{(m)}$ Reset the coordinates of the m+1 molecule according to $$r_j = (R_{\Omega m+1} r_j{}^o + r_{m-1} n_{m-1}) \qquad (24)$$

set M to m+1.
6. Repeat steps 4 and 5 until m=M−1.

The other uses the growth method of step (b) iteratively to create a polymer assembly.

The logic flow chart of FIG. 9 is a diagram of the excluded volume polymer assembly method. Rectangle 97 represents reading in from the polymer file which has a number of single polymer chains in the file. Rectangle 98 represents arbitrary choosing how to read the polymer chains in from the file using either a random number or to select a particular chain from the file. Rectangle 99 represents setting the origin of the system as the center of mass of the first chain. The oval 101 represents the selection of a second polymer from the determination. Rectangle 102 represents orientation of the polymer in all possible ways to eliminate all overlaps of atoms in the two structures and the two structures are as close as possible to each other without overlapping.

It is noted that there is no change in the internal angles of the polymer chain, but only rotation and twisting of the entire chain to avoid overlaps. This is computed using the equation of the article entitled "Molecular Silverware" (J. Computational Chemistry, Vol. 12, No. 2 pp. 237-247 (1991).

Rectangle 103 represents growing of the polymer cluster by adding the current molecule displaced from the center of the mass in the preceding step. Diamond 104 represents checking to determine whether the full assembly has been created. If yes, proceed to display of rectangle 105. If not, the program returns to oval 101.

From display at 105 the program proceeds to the question in diamond 106, are properties to be estimated. If yes, program proceeds to Step D, property estimation and analysis, block 19. The negative branch goes to diamond 107 for decision on the question, of choosing a different labeling scheme. An affirmative branches back to rectangle 99 and a negative to stop point 108. FIG. 10 is a block diagram illustrating the multi-chain growth method.

Estimation of the physical properties of the resulting clusters is achieved through the use of molecular energy expressions and/or quantitative structure property relationships, applied to the outcomes of steps (a), (b), and (c). Physical property estimation may also be achieved by any of the standard molecular modeling techniques, including but not limited to molecular mechanics, molecular dynamics, Monte Carlo methods, free energy perturbation methods, or the analytical vector geometry method described herein. Examples of properties computed are:

Thermal Properties: Glass Transition Temperature
Optical Properties: Refractive Index
Diffusion Properties: Specific Free Volume $CO_2$, $O_2$ Diffusion Coefficients
Mechanical Properties: Elastic Moduli The logic flow chart of FIG. 10 illustrates the operation of a Multichain-Growth Polymer Assembly Method, which uses the growth method to create an assembled polymer structure. Rectangle 109 represents selecting how large assembly should be, i.e. the number of chains. Rectangle 110 represents generating starting points over the surface of a sphere. Rectangle 111 represents the selection of growth method. For each chain one of the starting points is selected as represented by the rectangle 112. And a chain is grown into the sphere employing a suitable method in accordance with the above description.

The rectangle 113 represents the question, are the chains all finished? If yes, the program proceeds to Step D, property estimation and analysis. If no, the program lops back to oval 114 and an addition of a chain.

The process proceeds until all the starting points are used and the desired chains grown. At that point a polymer is completed.

The following Examples serve to demonstrate aspects of the present inventive process.

EXAMPLE 1

Estimation of chemical molecular composition of a polymer reacted from a monomer mixture of methyl acrylate (MA) and styrene (STY)

The chemical composition of a copolymer rarely remains constant both in its overall instantaneous monomer percent concentration and monomer sequence distribution, during the course of a polymerization reaction. The physical properties of the copolymer are highly dependent upon such chemical drifts. It is for this reason that the ability to estimate the molecular composition of a copolymer at different points during the reaction (percent conversion) is so important.

As an example, consider the copolymerization of methyl acrylate with styrene. The present invention used published chemical kinetics experimental information (in the form of Q and e values) to estimate the composition of the copolymer as a function of conversion. Two cases are presented:

Case a: The starting composition is a 50:50 mixture of MA and STY
Case b: The starting composition is a 23:77 mixture of MA and STY

| Case a: Input Information | | | | | | | |
|---|---|---|---|---|---|---|---|
| L | 2 | | (Lin/Pha/CPha) (# unique mons) | | | | |
| | 50 | | (chain length) | | | | |
| MA | | | (Monomer 1 Name) | | | | |
| | 1.0000 | 0.420 | 0.650 | 86.09 | 8.0 | 1.4800 | 1 |
| | (Conc | Q | E | MW | TG | RI | Frag) |
| STY | | | | | | | |
| | 1.0000 | 1.000 | −0.800 | 104.14 | 100.0 | 1.5900 | 31 |
| | (Conc | Q | E | MW | TG | RI | Frag) |
| M | | | (Mole or Weight Basis) | | | | |
| | −987765440 | | (Random # seed) | | | | |

Figure 11:
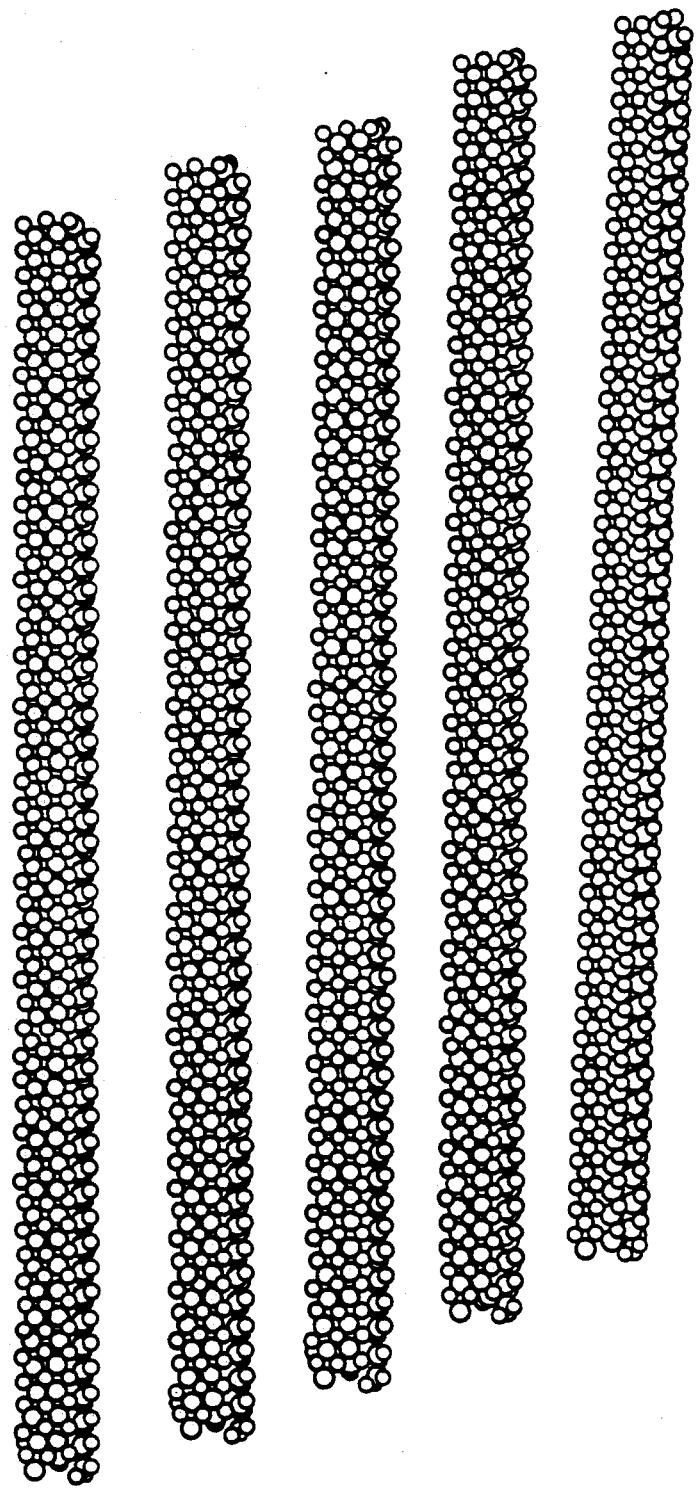
Figure 12:
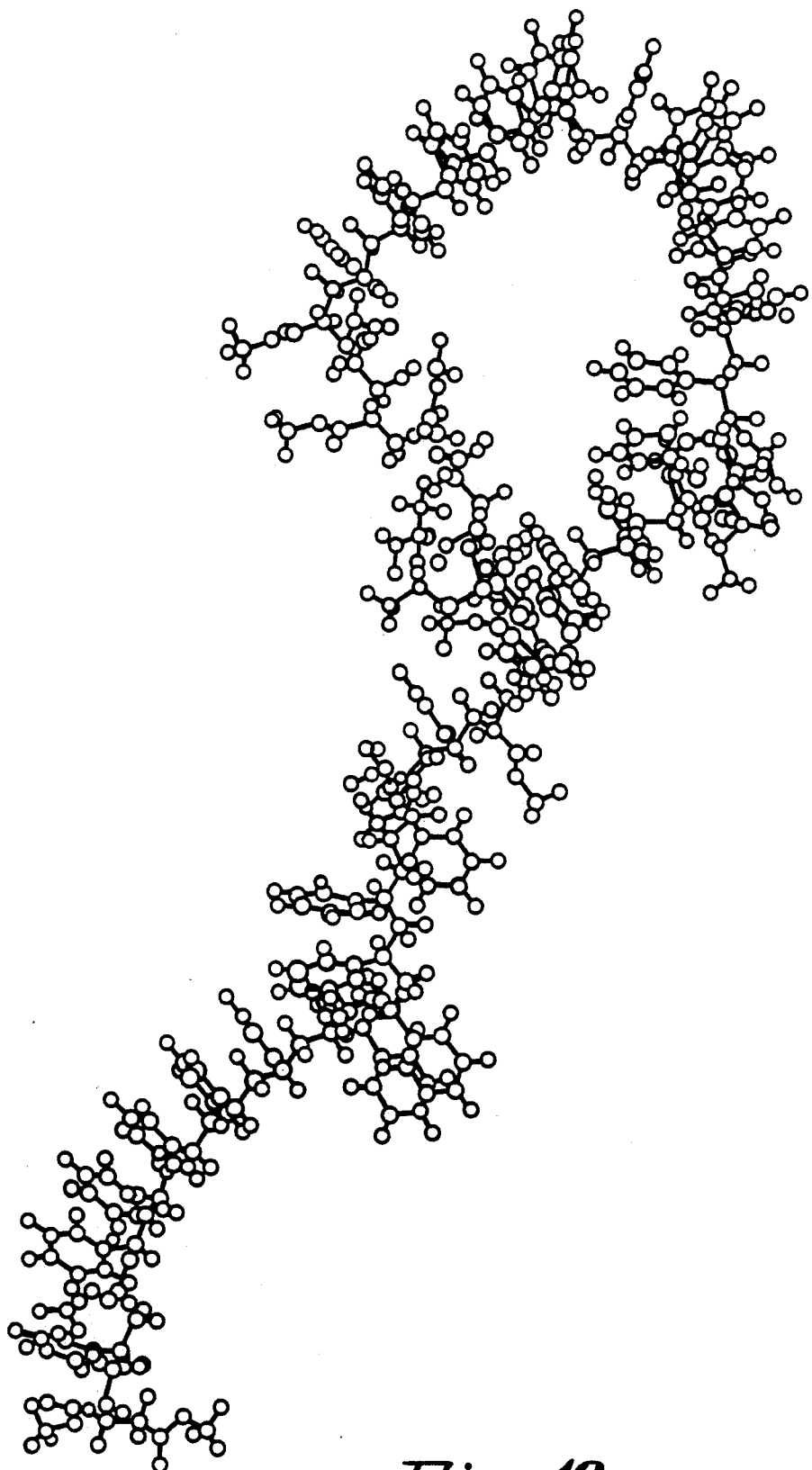
Figure 13:
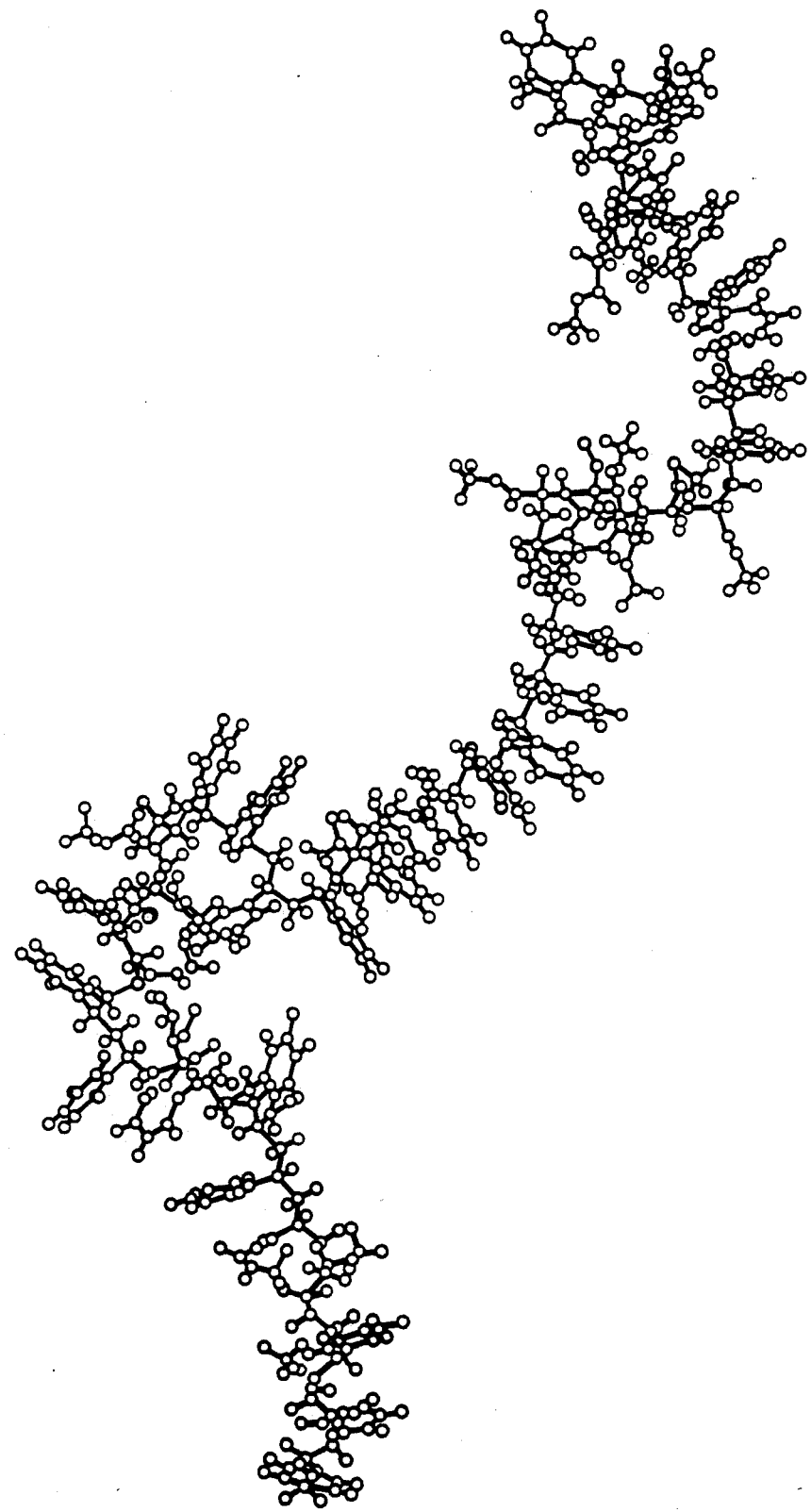
Figure 14:
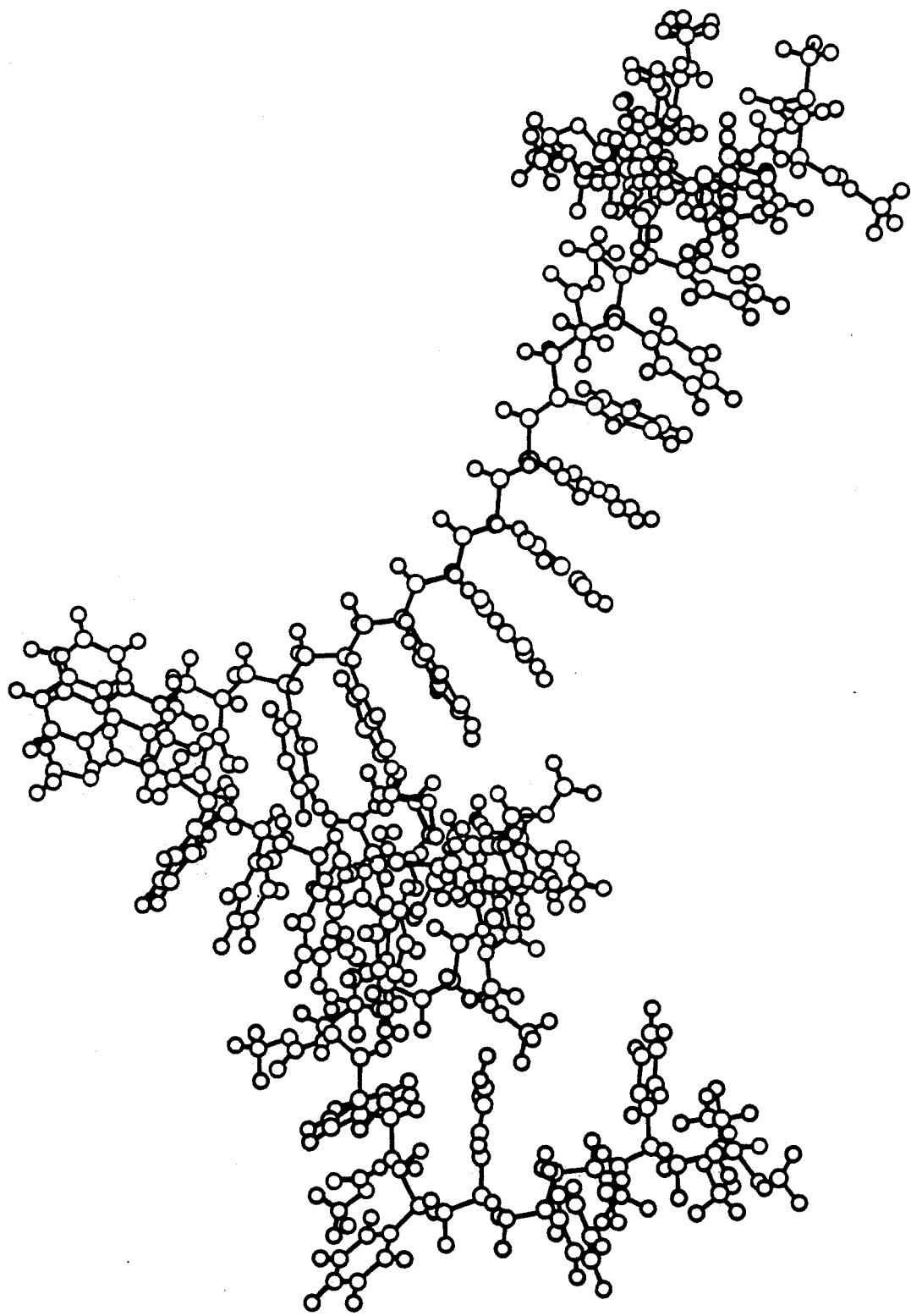
Figure 15:
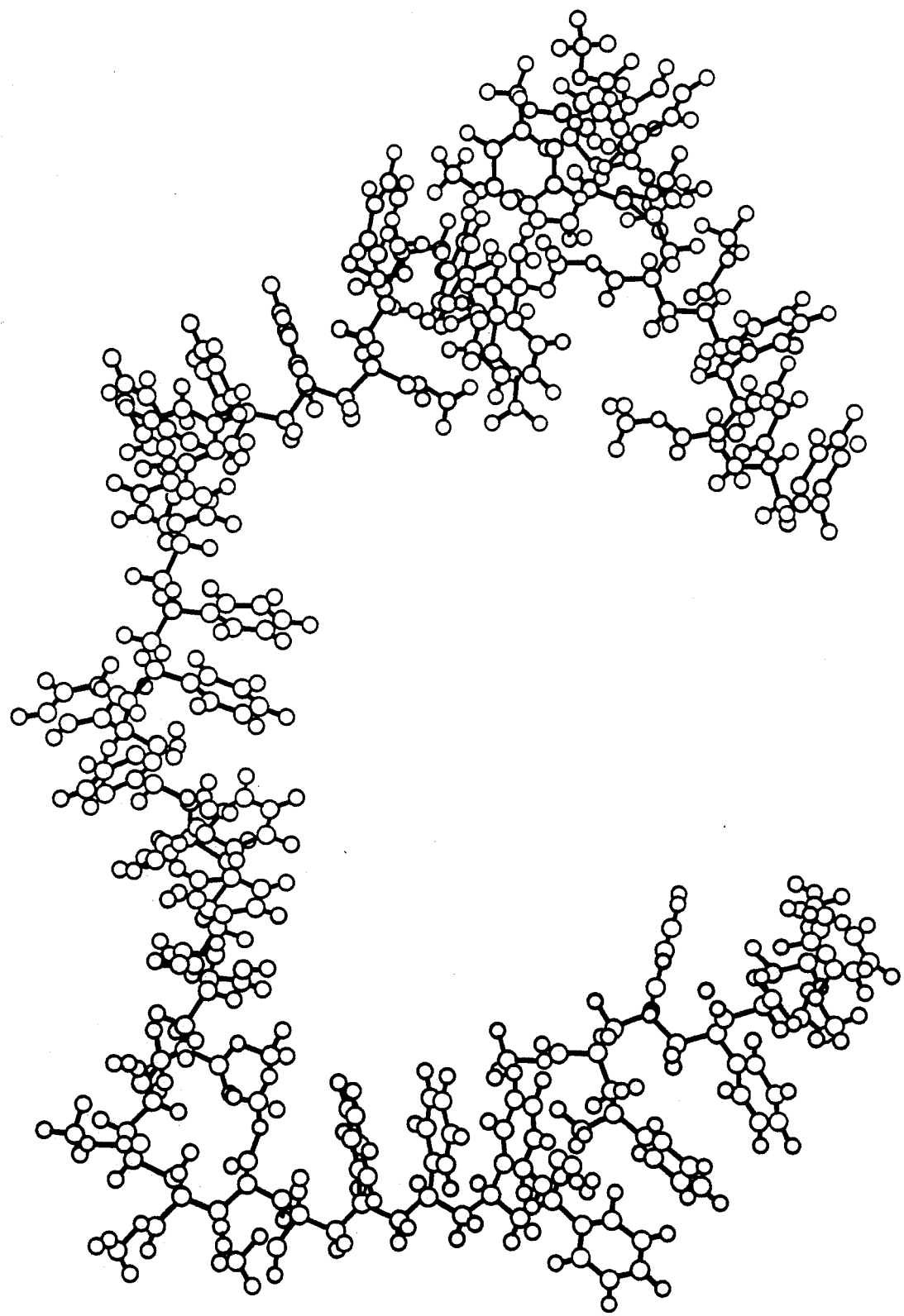
Figure 16:
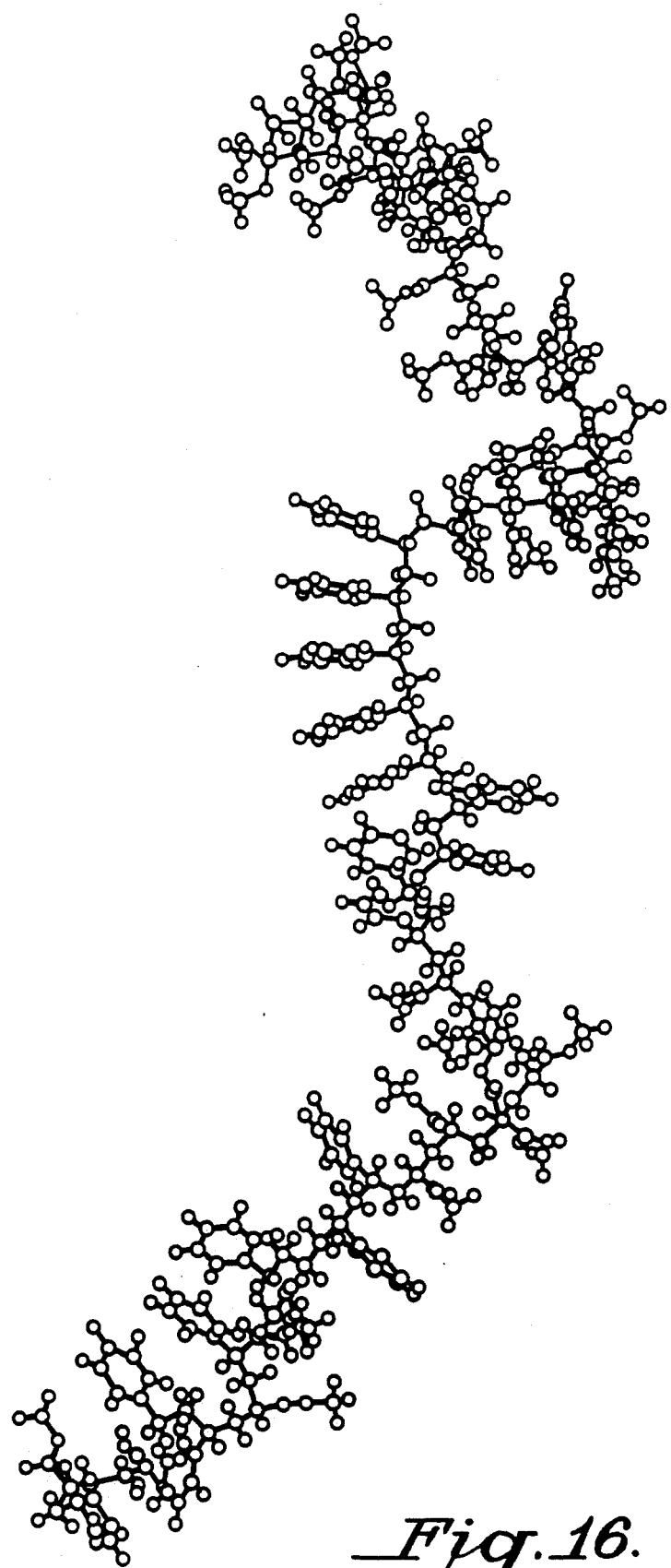

The first line refers to the type of polymer chain to be generated, i.e. In Situ, linear, Phantom, Conditional Phantom. Polymer examples having a length of 50 monomers were requested. FIG. 11 ia a computer generated picture of the instantaneous polymer composition as a function of monomer conversion. The conversion values are 0.0%, 25%, 50%, 75% and 100% from top to bottom respectively. Note the small drift in composition due to the differences in reactivities between the two monomers. This agrees with the experimental preparation of this polymer.

Using the In Situ methods, three dimensional structures of these copolymers were generated from Case a. FIGS. 12-17 show the structural variations of these differing sequences copolymer chains at the 0%, 20%, 40%, 60% 80% and 99% monomer conversion levels. With a 50:50 mixture of starting material, a very different set of structures were achieved during the course of a batch reaction. This leads to a wide variation in polymer shapes and compositions.

Figure 17:
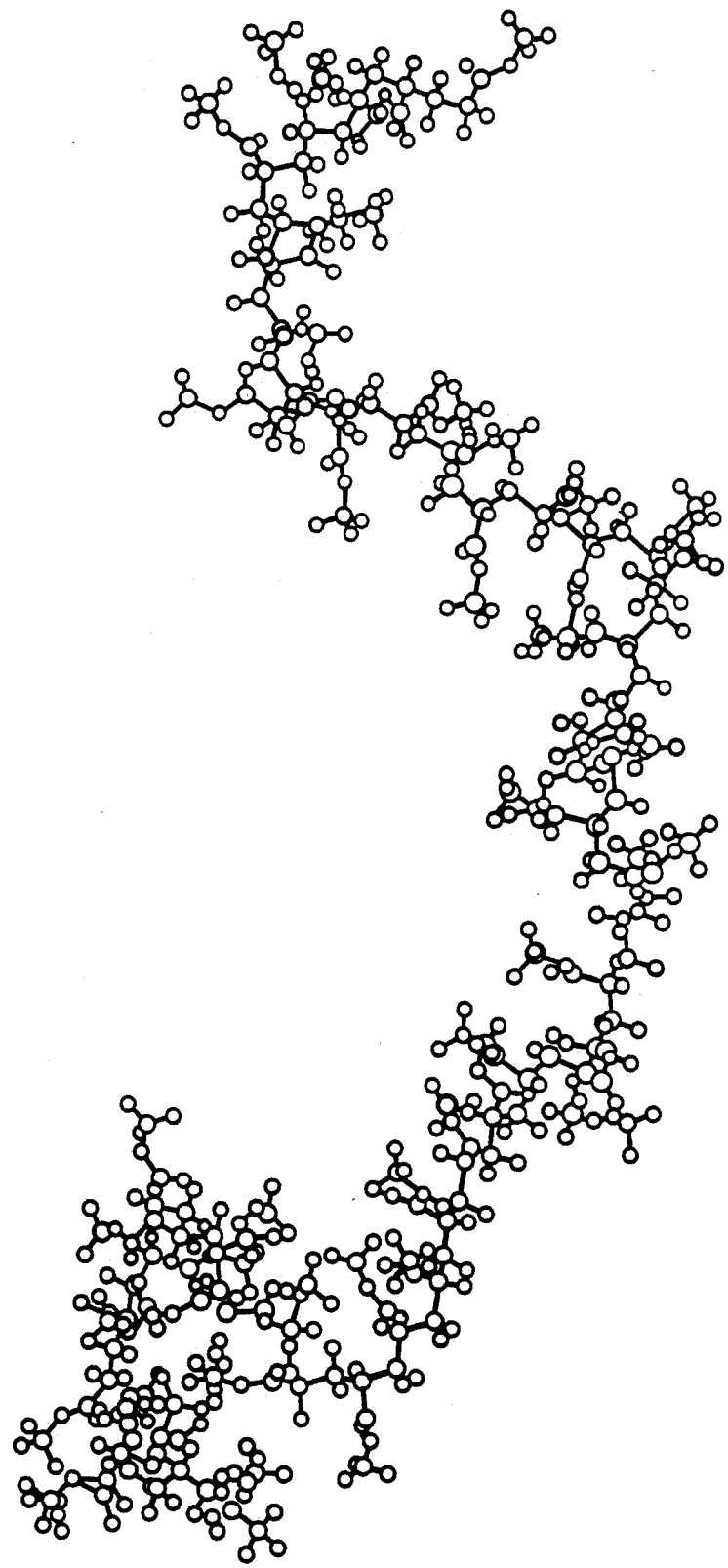

At the end of the reaction (close to 100% conversion), the copolymer that is being prepared is almost exclusively made up of methyl acrylate. Styrene has a larger preference for reacting with itself and it forms strings of connected styrene monomers even from the start of the reaction. At close to 100% conversion, most of the styrene has already been incorporated into the reacted polymer leaving only methyl acrylate to form polymer structures (FIG. 17).

| Output Information *Conversion-Composition (Mole Fraction Basis)* | | | | | | |
|---|---|---|---|---|---|---|
| # | Monomer Name | Q | E | MWT | TG | RI |
| 1: | MA | 0.420 | 0.650 | 86.09 | 8.0 | 1.4800 |
| 2: | STY | 1.000 | −0.800 | 104.14 | 100.0 | 1.5900 |

| Conversion | | Monomer Mix | Instantaneous Polymer | Cumulative Polymer |
|---|---|---|---|---|
| 0.000 | Monomer 1 | 0.5000 | 0.3798 | 0.3798 |
| | Monomer 2 | 0.5000 | 0.6202 | 0.6202 |
| | Glass Trans Temp (Deg C.) | | 63.0 | 63.0 |
| | Refractive Index | | 1.5530 | 1.5530 |
| 0.200 | Monomer 1 | 0.5283 | 0.3944 | 0.3867 |
| | Monomer 2 | 0.4717 | 0.6056 | 0.6133 |
| | Glass Trans Temp (Deg C.) | | 61.7 | 62.4 |
| | Refractive Index | | 1.5515 | 1.5523 |
| 0.400 | Monomer 1 | 0.5697 | 0.4158 | 0.3955 |
| | Monomer 2 | 0.4303 | 0.5842 | 0.6045 |
| | Glass Trans Temp (Deg C.) | | 59.7 | 61.6 |
| | Refractive Index | | 1.5493 | 1.5514 |

-continued

| | | | | | |
|---|---|---|---|---|---|
| 0.600 | Monomer 1 | | 0.6384 | 0.4526 | 0.4077 |
| | Monomer 2 | | 0.3616 | 0.5474 | 0.5923 |
| | Glass Trans Temp (Deg C.) | | | 56.2 | 60.4 |
| | Refractive Index | | | 1.5453 | 1.5501 |
| 0.800 | Monomer 1 | | 0.7862 | 0.5502 | 0.4285 |
| | Monomer 2 | | 0.2138 | 0.4498 | 0.5715 |
| | Glass Trans Temp (Deg C.) | | | 47.3 | 58.5 |
| | Refractive Index | | | 1.5347 | 1.5479 |
| 0.990 | Monomer 1 | | 1.0000 | 1.0000 | 0.4949 |
| | Monomer 2 | | 0.0000 | 0.0000 | 0.5051 |
| | Glass Trans Temp (Deg C.) | | | 8.0 | 52.3 |
| | Refractive Index | | | 1.4800 | 1.5408 |

Case b:
Input Information

| | | | | | | | |
|---|---|---|---|---|---|---|---|
| L | | | | | | | (Lin/Pha/CPha) |
| 2 | | | | | | | (# unique mons) |
| 50 | | | | | | | (chain length) |
| MA | | | | | | | (Monomer 1 Name) |
| 0.233 | 0.420 | 0.650 | 86.09 | 8.0 | 1.4800 | 1 | (Conc Q E MW TG R |
| STY | | | | | | | (Monomrt 2 Name) |
| 0.767 | 1.000 | −0.800 | 104.14 | 100.0 | 1.5900 | 31 | (Conc Q E MW TG R |
| M | | | | | | | (Mole or Weight B |
| −987765440 | | | | | | | (Random # seed) |

Only the initial monomer concentrations have been changed (methyl acrylate 0.233, styrene 0.767). Note that the drift in composition is drastically reduced when the initial monomer feed composition is changed from 50%:50% to 23.3%:76.7%. In fact, this composition is called the "azeotropic" composition. An azeotropic composition is that which balances the differences in reactivities of the two monomers by setting their initial concentrations such that at all times during the reaction the copolymer composition remains constant.

Figure 18:
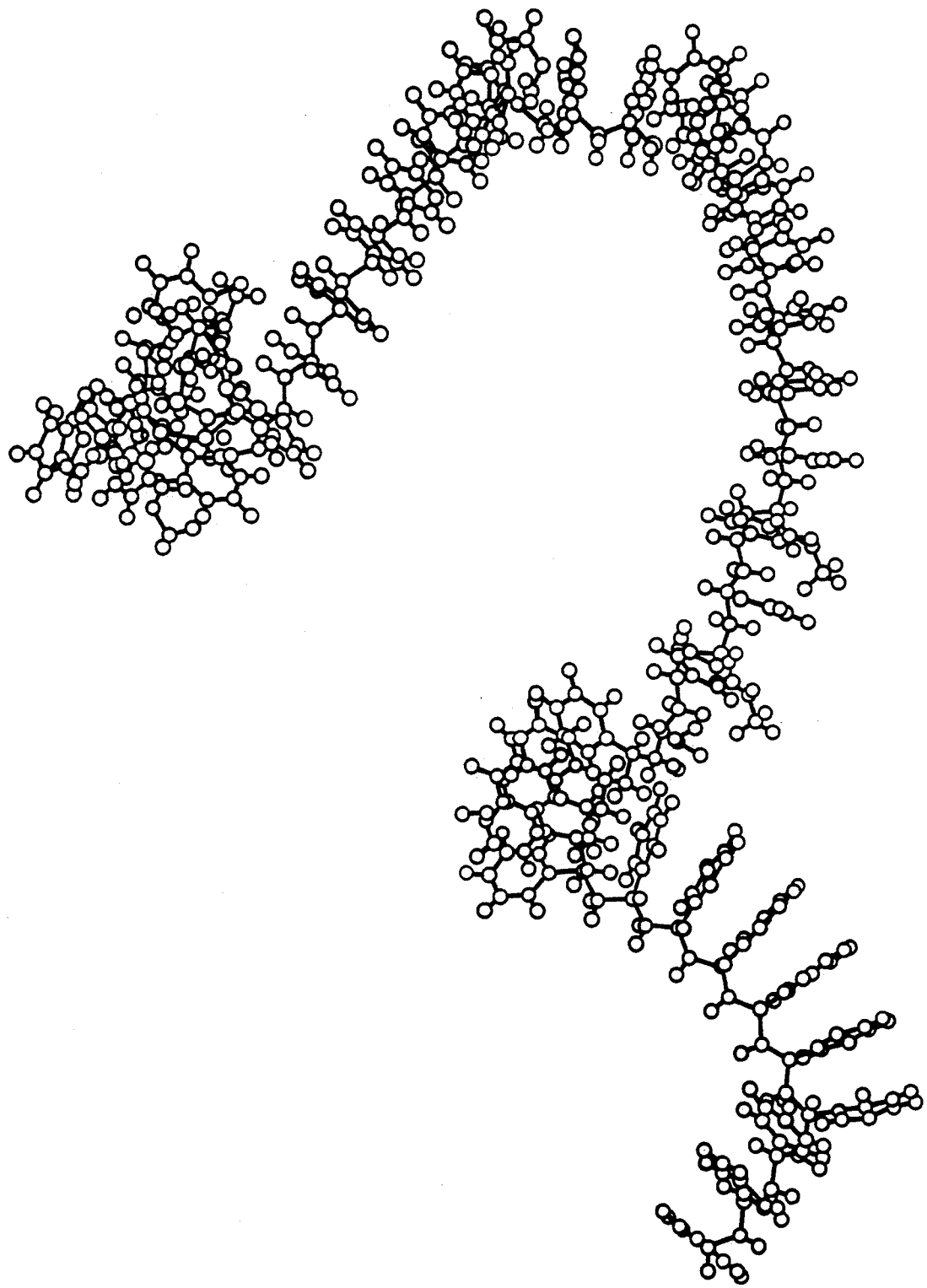
FIG. 18. is a computer generated picture of the resulting polymer wherein the starting materials are a 23.3:76.7 mixture of methyl acrylate (MA) and styrene (STY) in accordance with Example 1, case b.
Figure 19:
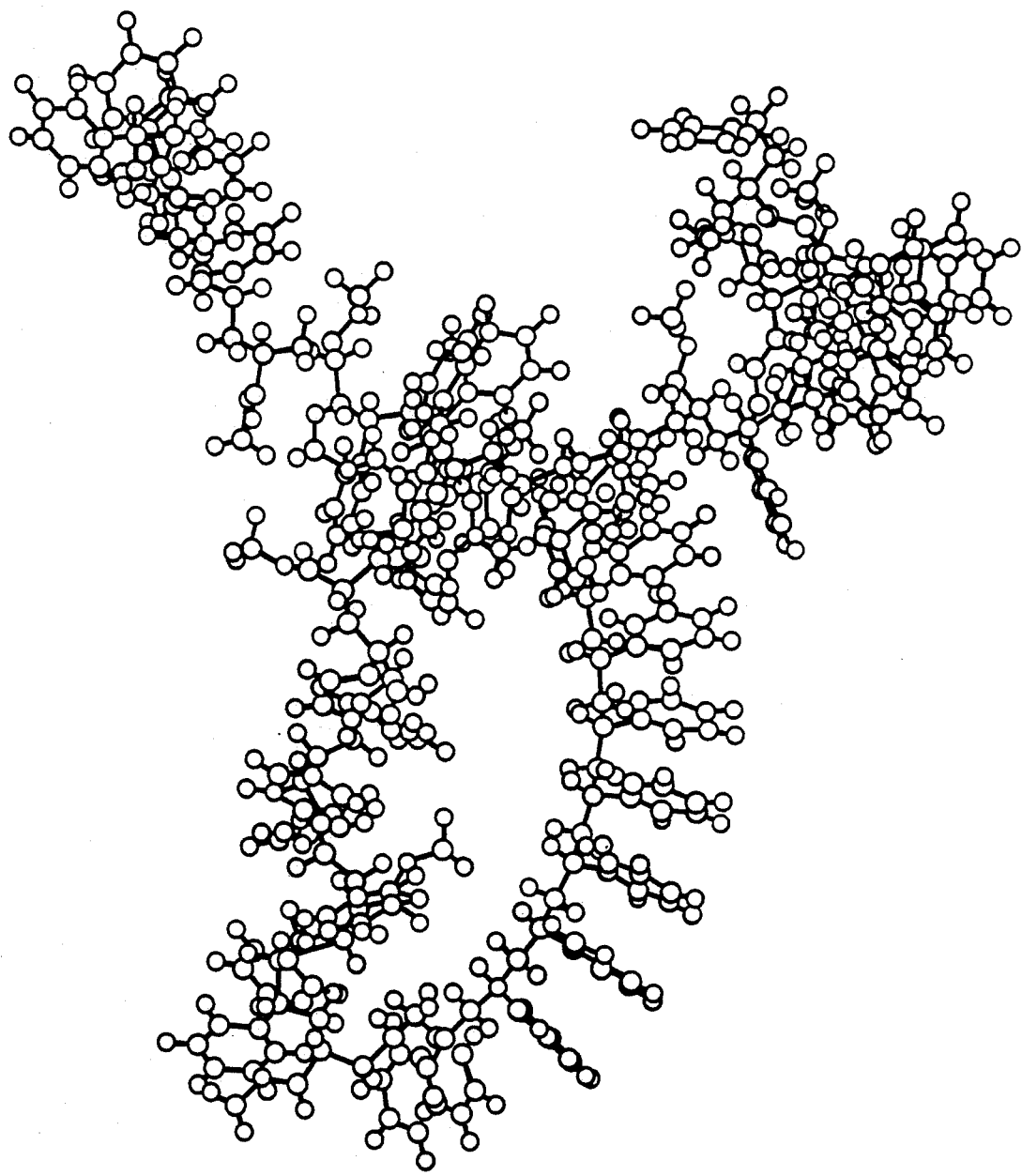
FIG. 19. is a computer generated picture of the resulting polymer wherein the starting materials are a 23.3:76.7 mixture of methyl acrylate (MA) and styrene (STY) at 99% conversion in accordance with Example 1, case b.

FIG. 18 shows the copolymer generated from example 1.b. In this case the polymer sequences and structures are the same throughout most of the reaction. Consequently, FIG. 18 is a polymer structure generated at all of the conversion levels 20%, 40%, 60% and 80%. The structure slightly changes at 99% and is shown in FIG. 19. The identical sequences and their similar three dimensional shapes create uniform polymer shapes and compositions during the course of the batch reaction.

The present invention allows for the location of such azeotropic compositions over all or just part of the polymer reaction. This invention also shows the differing polymer shapes and consequently describes many of their properties such as size, volume, stiffness, and polymer structure. From these structures many other polymer design problems may be considered, such as packing, tensile strength, glass transition temperature, and other polymer properties which rely on the inherent three dimensional shape of polymers.

Output Information
*Conversion-Composition (Mole Fraction Basis)*

| # | Monomer Name | Q | E | MWT | TG | RI |
|---|---|---|---|---|---|---|
| 1: | MA | 0.420 | 0.650 | 86.09 | 8.0 | 1.4800 |
| 2: | STY | 1.000 | −0.800 | 104.14 | 100.0 | 1.5900 |

| Conversion | | Monomer Mix | Instantaneous Polymer | Cumulative Polymer |
|---|---|---|---|---|
| 0.000 | Monomer 1 | 0.2330 | 0.2243 | 0.2243 |
| | Monomer 2 | 0.7670 | 0.7757 | 0.7757 |
| | Glass Trans Temp (Deg C.) | | 77.8 | 77.8 |
| | Refractive Index | | 1.5688 | 1.5688 |
| 0.200 | Monomer 1 | 0.2350 | 0.2257 | 0.2250 |
| | Monomer 2 | 0.7650 | 0.7743 | 0.7750 |
| | Glass Trans Temp (Deg C.) | | 77.7 | 77.8 |
| | Refractive Index | | 1.5686 | 1.5687 |
| 0.400 | Monomer 1 | 0.2378 | 0.2277 | 0.2258 |
| | Monomer 2 | 0.7622 | 0.7723 | 0.7742 |
| | Glass Trans Temp (Deg C.) | | 77.5 | 77.7 |
| | Refractive Index | | 1.5684 | 1.5686 |
| 0.600 | Monomer 1 | 0.2422 | 0.2307 | 0.2269 |
| | Monomer 2 | 0.7578 | 0.7693 | 0.7731 |
| | Glass Trans Temp (Deg C.) | | 77.2 | 77.6 |
| | Refractive Index | | 1.5681 | 1.5685 |
| 0.800 | Monomer 1 | 0.2510 | 0.2368 | 0.2285 |
| | Monomer 2 | 0.7490 | 0.7632 | 0.7715 |
| | Glass Trans Temp (Deg C.) | | 76.6 | 77.4 |
| | Refractive Index | | 1.5675 | 1.5684 |
| 0.990 | Monomer 1 | 0.3253 | 0.2843 | 0.2321 |
| | Monomer 2 | 0.6747 | 0.7157 | 0.7679 |
| | Glass Trans Temp (Deg C.) | | 72.1 | 77.1 |
| | Refractive Index | | 1.5628 | 1.5680 |

EXAMPLE 2

Estimation of the Gas Permeation Properties of Packaging Material Containing Para-Hydroxy Styrene (PHS)

A series of para-substituted polystryenes investigated to study the effect of chemical composition of free volume (Table I).

TABLE I

Modeled Substituted Polystyrenes

| POLYMER | | X | Density (gr/cc) | Calculated Free Volume (cc/gr) |
|---|---|---|---|---|
| Poly(p-chlorostyrene) | PCS | —Cl | 1.246 | 0.262 |
| Poly(p-hydroxystyrene) | PHS | —OH | 1.173 | 0.274 |
| Poly(p-fluorostyrene) | PFS | —F | 1.176 | 0.292 |
| Poly(p-methoxystyrene) | PMxS | —OCH3 | 1.118 | 0.295 |
| Poly(p-acetoxystyrene) | PAS | —OCOCH3 | 1.168 | 0.297 |
| Poly(alpha-methylstyrene) | PaMS | —H (a) | 1.065 | 0.299 |
| Polystyrene | PS | —H | 1.048 | 0.325 |
| Poly(p-methylstyrene) | PMS | —CH3 | 1.009 | 0.346 |
| Poly(p-t-butylstyrene) | PtBS | —C(CH3)3 | 0.947 | 0.396 |

Figure 20:
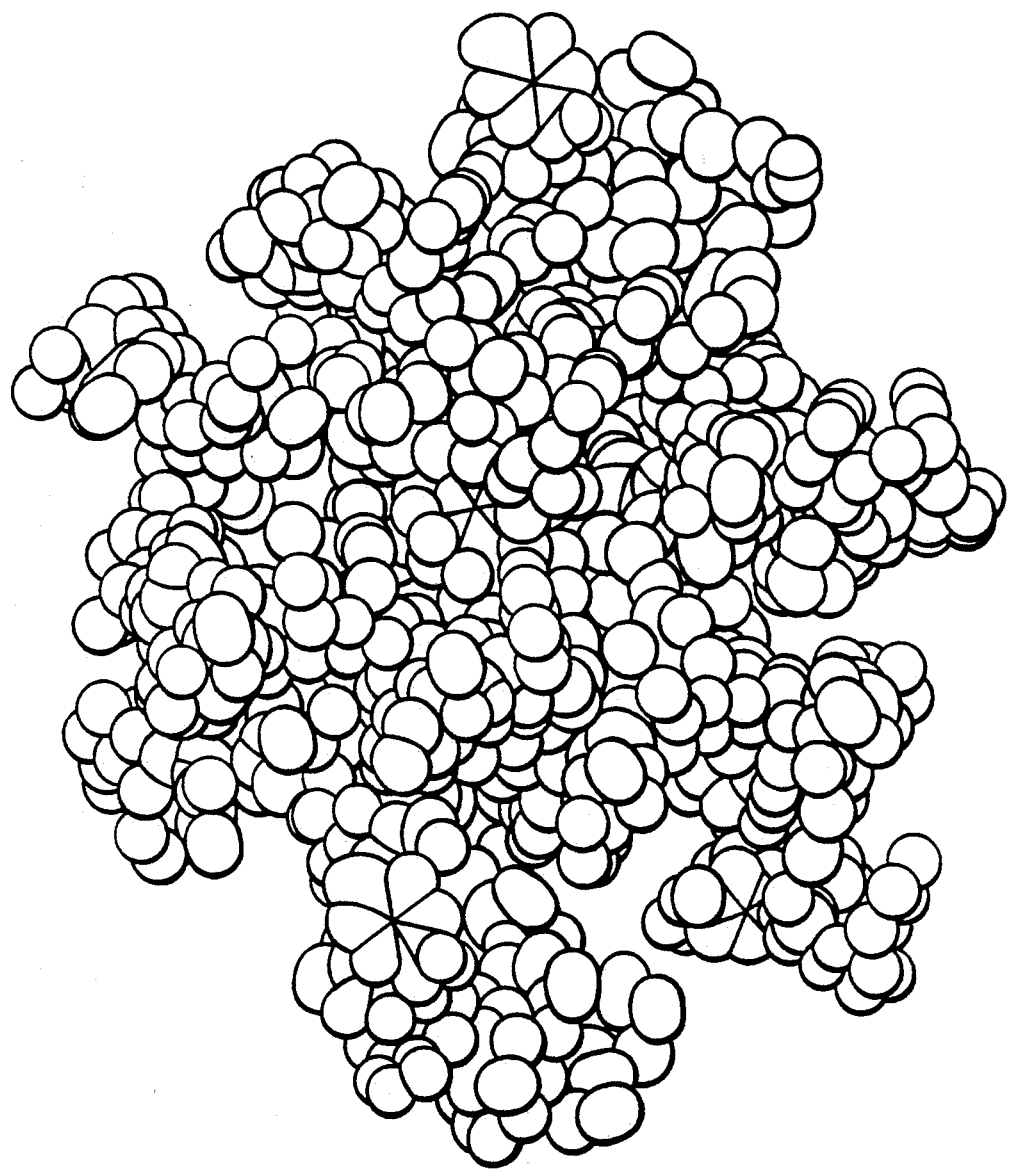
FIG. 20. is an example of (PHS) of the polymer clusters modeled in accordance with Example 2.

For each of these polymer, the process of the instant invention was implemented. The degree of packing in the assembled cluster estimated in Step (d) also utilized the following expression:

$$Vf\,(calculated) = 1/d - No\,Vc/Mc \qquad (3)$$

where "d" is the polymer's experimental density, "No" Avogadro's number, "Mc" and "Vc" the calculated mass and molar volume occupied by the assembly of polymer molecules. FIG. 20 shows an example (PHS) of the polymer clusters modeled with the invention and used to calculate the quantities Mc and Vc in formula (3).

Figure 21:
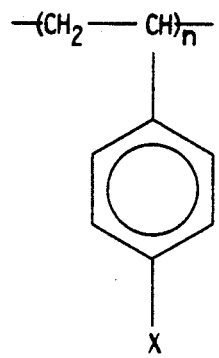
FIG. 21. is a graph of projected free volume values versus group additivity free volumes in accordance with Example 2.
Figure 21:
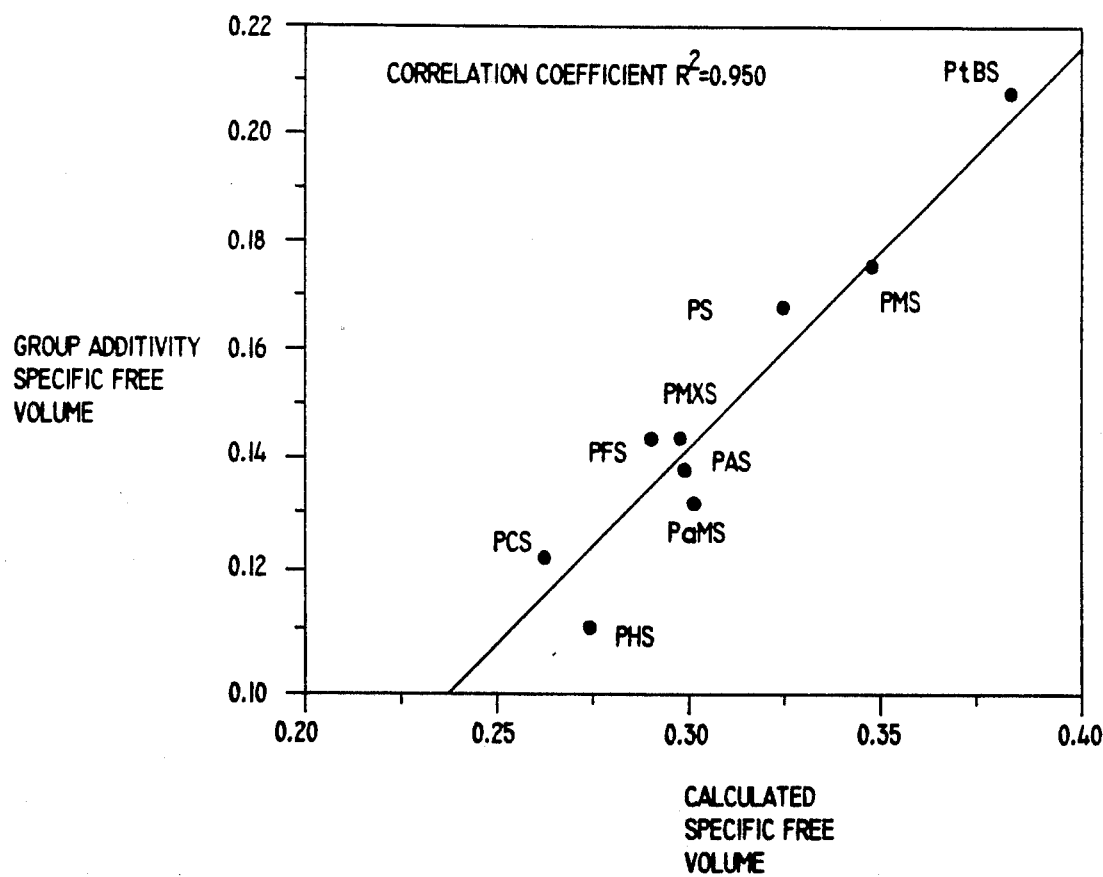

Table I shows the calculated void volume values for the family of para-substituted polystyrenes. FIG. 21 shows a comparison of the instant application's projected free volumes with those obtained using the experimentally based method commonly referred in the literature as "group additivity". Dirk W. van Krevelen, "Properties of Polymers, Their Estimation and Correlation with Chemical Structure", 2nd edition, Elsevier Science Publishers B.V., 1987. Applicants' predictions and the group additivity results are in good qualitative agreement. From the results one would conclude that among the para-substituted polystyrenes PHS has a low permeability because its void volume is among the lowest of the para-substituted styrenes while PtBS should have one of the highest permeabilities by virtue of its high free volume value.

The predictions of the modeling of the instant invention were then compared against experimental data. The system of para-substituted polystyrenes has since been studied by Prof. Donald R. Paul, at the University of Texas at Austin. Puleo A. C., Muruganandam N., Paul, D. R. "Gas Sorption and Transport in Substituted Polystyrenes", Journal of Polymer Science Part B-Polymer Physics, 1989, V27, N11, pp. 2385–2406. Comparison was based upon a well known expression relating gas permeability and free volume values:

$$P = P_o\,exp\,(-V_o/Vf) \qquad (4)$$

Taking logarithms on both sides of this expressions one should obtain straight lines when plotting Log P vs Log (1/Vf). The lines were fitted with a simple expression of the form:

$$Log\,P\,(experimental) = Log\,P_o - V_o/Vf\,(calculated) \qquad (5)$$

where $P_o$ and $V_o$ are constants which depend only on the type of diffusing gas, e.g. oxygen or carbon dioxide. The experimental vs. projected values are shown in Tables II.A and II.B for oxygen and carbon dioxide respectively. The Experimental values are obtained from the Paul article. Table III contains the values of the constants in the permeability model.

TABLE II.A

Experimental vs. Calculated (Eq. 4) Oxygen Permeability Values

| | | | $PO_2$[1] | |
|---|---|---|---|---|
| POLYMER | | X | Exp. | Pred. |
| Poly(p-chlorostyrene) | PCS | —Cl | 1.20 | 0.4357 |
| Poly(p-hydroxystyrene) | PHS | —OH | 0.12 | 0.7424 |
| Poly(p-fluorostyrene) | PFS | —F | 4.40 | 1.5214 |
| Poly(p-methoxystyrene) | PMxS | —OCH3 | 2.60 | 1.7001 |
| Poly(p-acetoxystyrene) | PAS | —OCOCH3 | 3.10 | 1.8284 |
| Poly(alpha-methyl-styrene) | PaMS | —H (a) | 0.82 | 1.9646 |
| Polystyrene | PS | —H | 2.90 | 4.6111 |
| Poly(p-methylstyrene) | PMS | —CH3 | 7.20 | 8.3645 |
| Poly(p-t-butylstyrene) | PtBS | —C(CH3)3 | 35.50 | 26.7805 |

[1] $10^{}$-10 [cc(STP)cm/cm$^{}$2 sec cm Hg]

TABLE II.B

Experimental vs. Calculated (Eq. 4) Carbon Dioxide Permeability Values

| | | | $PO_2$[1] | |
|---|---|---|---|---|
| POLYMER | | X | Exp. | Pred. |
| Poly(p-chlorostyrene) | PCS | —Cl | 4.3 | 3.7303 |
| Poly(p-hydroxystyrene) | PHS | —OH | — (2) | 5.6067 |
| Poly(p-fluorostyrene) | PFS | —F | 17.2 | 9.7025 |
| Poly(p-methoxystyrene) | PMxS | —OCH3 | 18.9 | 10.5622 |
| Poly(p-acetoxystyrene) | PAS | —OCOCH3 | 16.3 | 11.1666 |
| Poly(alpha-methyl-styrene) | PaMS | —H (a) | 3.0 | 11.7968 |
| Polystyrene | PS | —H | 12.4 | 22.6472 |
| Poly(p-methylstyrene) | PMS | —CH3 | 29.8 | 35.7041 |
| Poly(p-t-butylstyrene) | PtBS | —C(CH3)3 | 140.1 | 86.9049 |

[1] $10^{}$-10 [cc(STP)cm/cm$^{}$2 sec cm Hg]
[2] not measured by D. Paul

TABLE III

Gas Permeability Model Parameters

| GAS | | Po (1) | Vo (2) |
|---|---|---|---|
| Oxygen | O2 | 11.340 | 3.188 |
| Carbon Dioxide | CO2 | 10.620 | 2.437 |

(1) $10^{}$-10 [cc(STP)cm/cm$^{}$2 sec cm Hg)
(2) cc/gr

Figure 22:
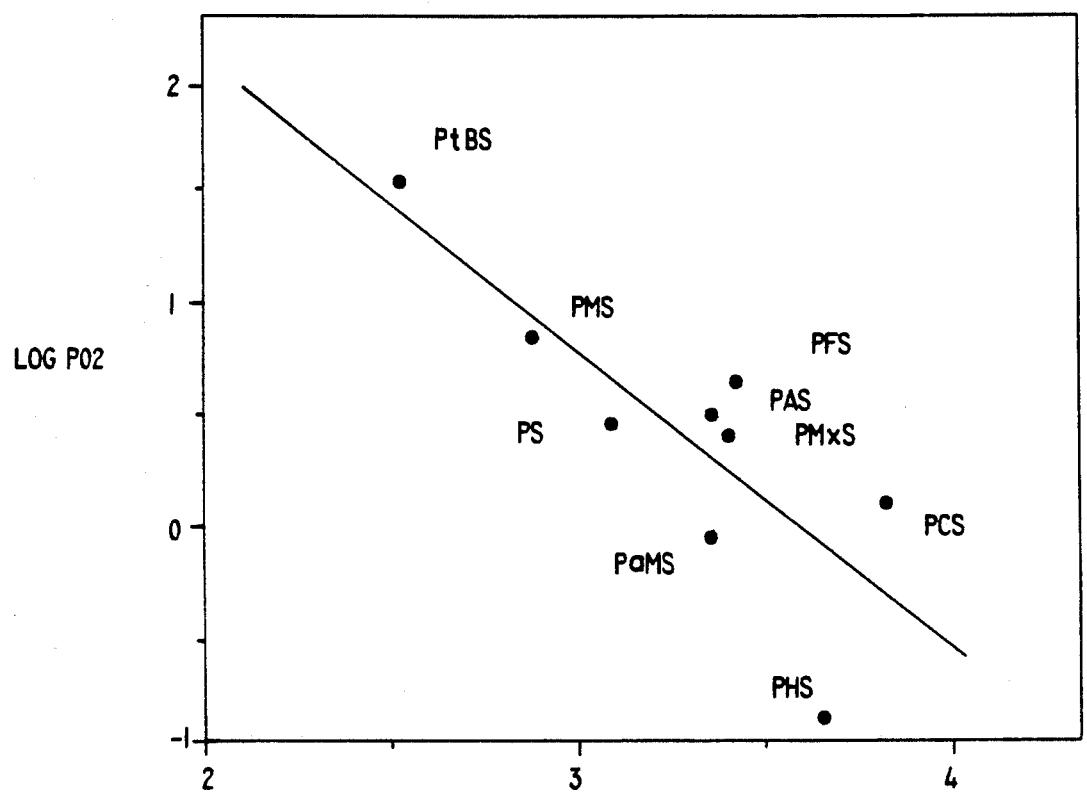
FIG. 22. is a graph of projected free volume values versus the Log of experimentally obtained Oxygen Permeability in accordance with Example 2.
Figure 23:
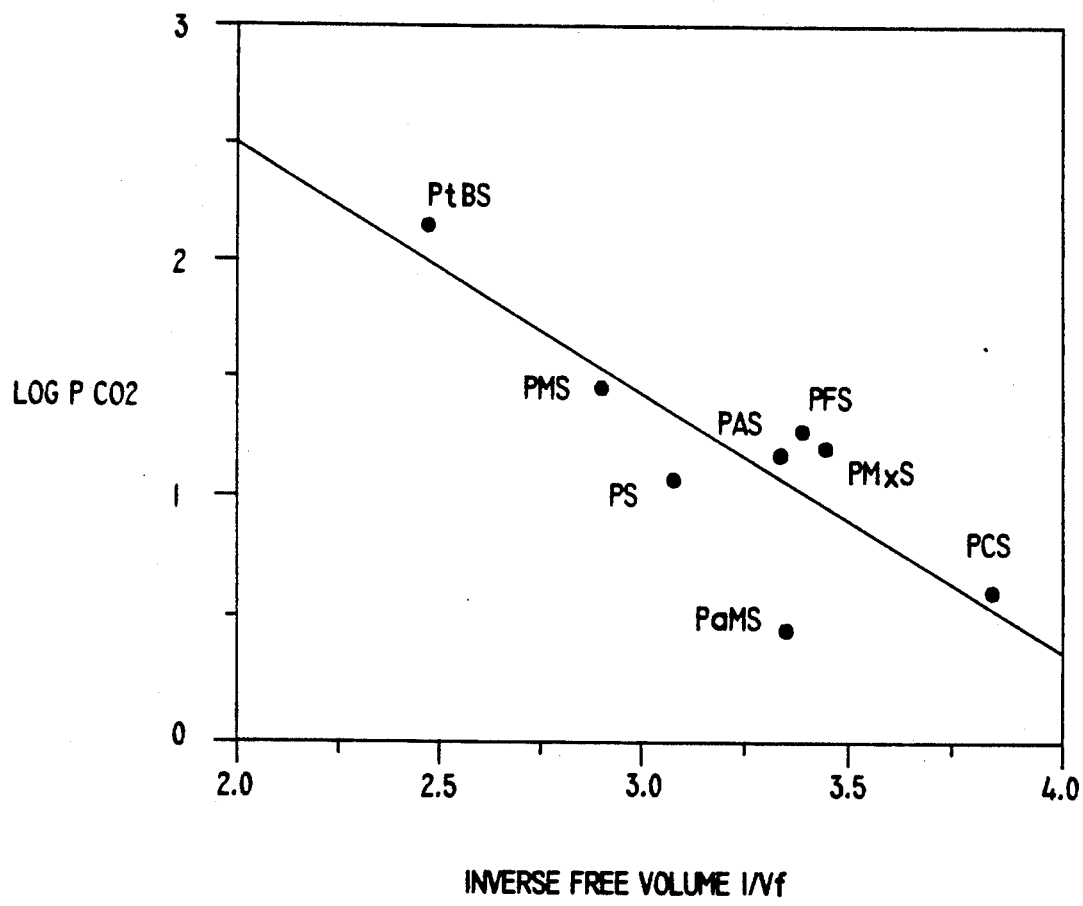
FIG. 23. is a graph of projected free volume values versus the Log of experimentally obtained $CO_2$ permeability in accordance with Example 2.

FIG. 22 illustrates graphically the qualitative agreement between the model's predictions (Vf) and the experimental permeability results. Similar results are obtained for carbon dioxide permeability values (FIG. 23). The fits indicate that the calculated Vf values are in good qualitative agreement with the experimentally measured gas permeabilities. Note in particular that the projections concerning the permeabilities of PHS and PtBS were confirmed by Prof. D. Paul's studies. PHS gives the lowest oxygen permeability values across the family of substituted styrenes while PtBS gives the highest value. Furthermore, it is clear that the low permeability of PHS is due greatly to a highly reduced polymer void volume, a quantity that is calculated using the polymer modeling methods of the instant invention.

EXAMPLE 3

Copolymerization Kinetics of Acrylic Acid (AA) with Sodium Acrylate (NaA) Using N,N'-Methylenebis(Acrylamide) (MBAM) and Ethylene Glycol Dimethacrylate (EGDMA) as Crosslinkers This Example demonstrates the use of the present invention to determine a suitable crosslinker for the copolymerization of Acrylic Acid with Sodium Acrylate. One wishes the crosslinker to be incorporated into the copolymer in a more or less uniform way throughout the reaction. Table II shows the estimated compositional drifts that should be observed with EGDMA as the crosslinker with a starting composition of

Figure 24:
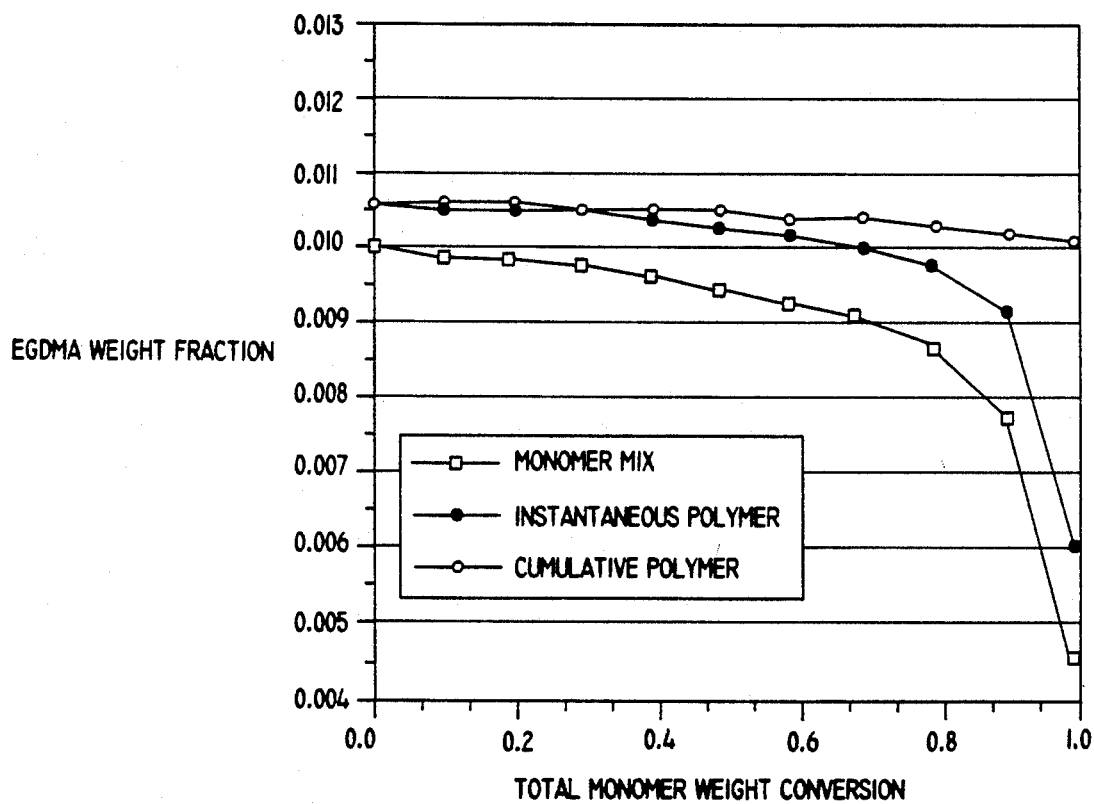
FIG. 24. is a graph of EGDMA weight fraction versus weight conversion, wherein the EGDMA monomer feed, the instantaneous, and the cumulative polymer compositions are shown as a function of total monomer weight conversion.
Figure 25:
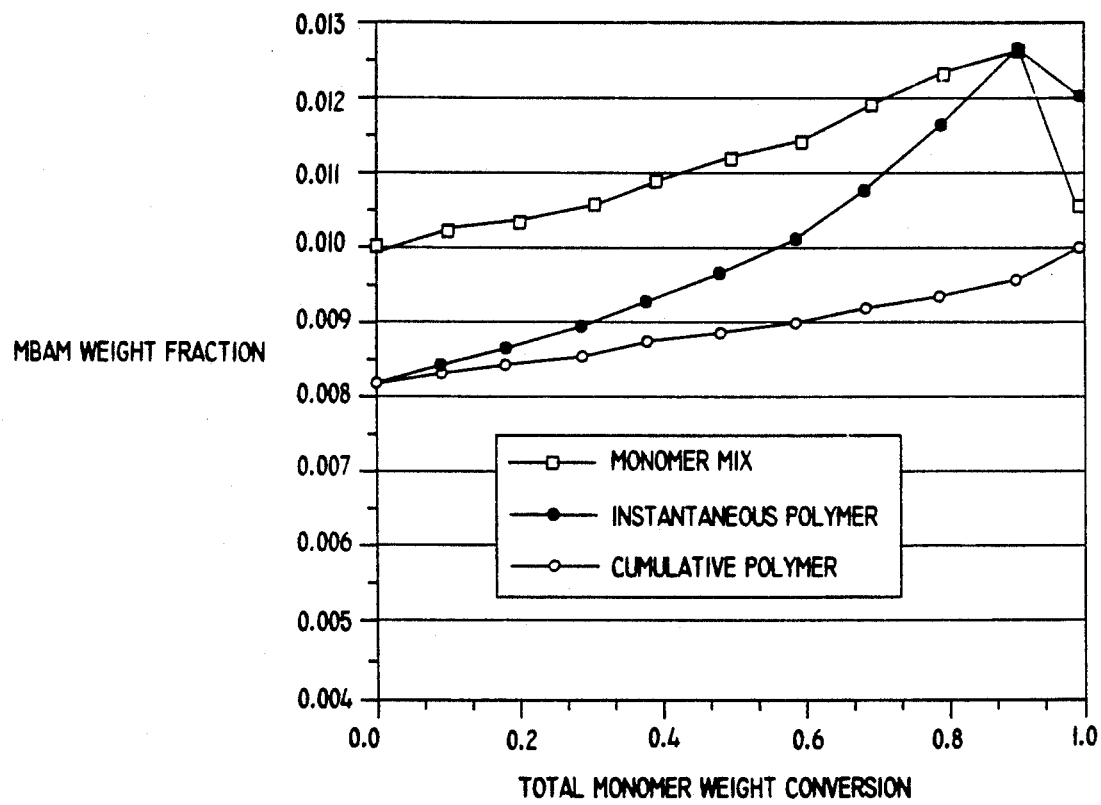
FIG. 25. is a graph of MBAM weight fraction versus weight conversion, wherein the MBAM monomer feed and the instantaneous and cumulative polymer compositions are shown as a function of total weight conversion.

*AA/NaA/EGDMA:22/77/1* by weight. FIG. 24 is a graph of EGDMA weight fraction versus weight conversion. The EGDMA monomer feed and the instantaneous and cumulative polymer compositions are shown as a function of total monomer weight conversion. Note that the instantaneous copolymer composition at 90% conversion suffers an 8% depletion in EGDMA compared to the starting composition. Depletion of EGDMA continues and reaches 40% at 99% conversion.

Crosslinker compositional drifts may be undesirable in such instances. The MBAM crosslinker is a better choice if one wishes the crosslinker to become incorporated into the polymer at a more uniform rate. Table III shows that for the same polymerization reaction the MBAM crosslinker drifts by less than 26% during the entire reaction. Based upon this chemical composition estimate, one would conclude that MBAM is a better choice of crosslinking agent.

More detailed compositional information can also be estimated with the present invention. Table IV shows the chemical sequence distribution (Dyads, Triads, and monotonic sequences of length up to 20) for the AA/NaA/MBAM terpolymer as a function of conversion. Notice that the MBAM crosslinker (C) reacts five times more often with Sodium Acrylate (B) than with Acrylic Acid (A). For example, at 90% conversion the dyad distributions are $AC+CA=0.171\%$ and $BC+CB=0.935\%$. This is not just the effect of the large concentration of Sodium Acrylate in the starting composition (77%) but also the result of the differences in the binary reactivity ratios. Table V shows these values. R1 is the ratio of reactivity of monomer 1 toward itself to the reactivity of monomer 1 toward monomer 2 ($R1=k11/k12$, $R2=k22/k21$). Thus, MBAM is 1.5 times ($R2'/R2''$) more reactive toward Sodium Acrylate than toward Acrylic Acid.

Figure 26:
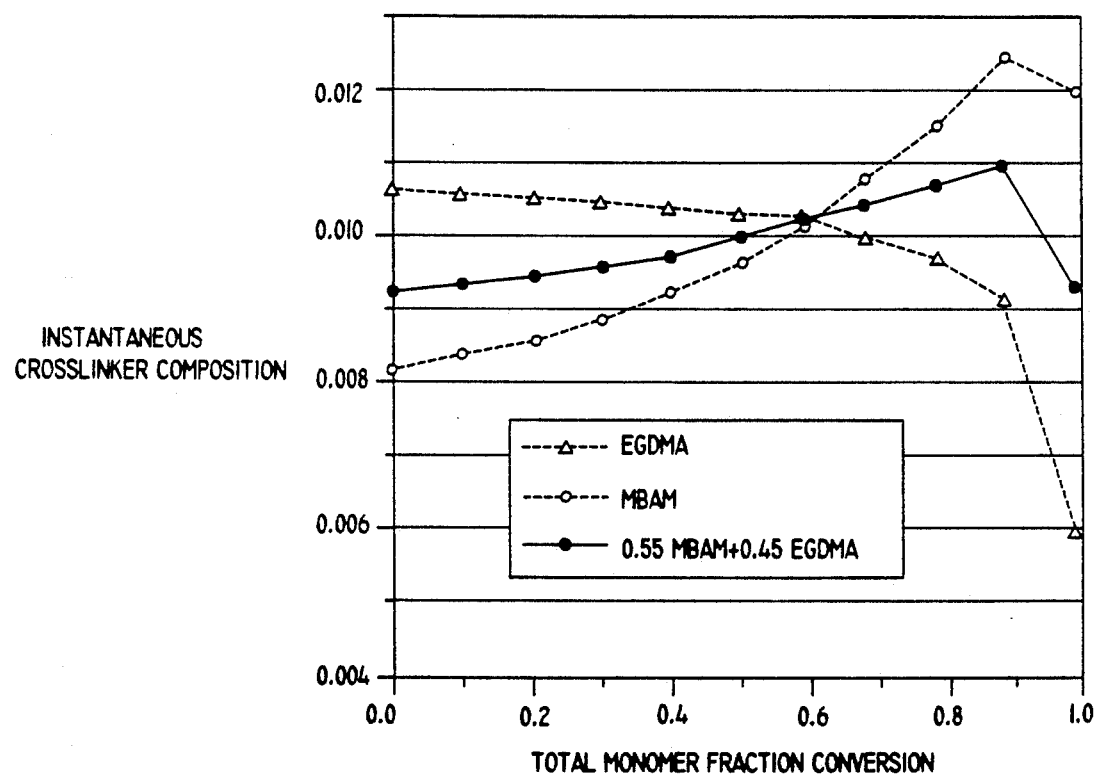
FIG. 26. is a graph of weight fraction composition for a mixture of EGDMA and MBAM crosslinkers as a function of conversion in accordance with Example 3.

Finally, one may choose a balanced mixture of these two crosslinkers to obtain a more uniform incorporation of crosslinker throughout the reaction. FIG. 26 shows the instantaneous polymer composition for a mixture consisting of 0.55% MBAM and 0.45% EGDMA. Note that because the individual crosslinking agents have opposite trends in their reactivities as a function of conversion, the selected mixture comes very close to the desired uniform incorporation of crosslinking agent throughout the entire conversion range.

TABLE II

Ternary Copolymer Kinetics for AA/NaA/EGDMA

Starting Composition: 22/77/1:AA/NaA/EGDMA

| MONOMER NAME | Q | E | Molecular Weight |
|---|---|---|---|
| MONO 1 AA | 1.1500 | 0.7700 | 72.06 |
| MONO 2 NAA | 0.7100 | −0.1200 | 94.05 |
| MONO 3 EGDMA | 0.8800 | 0.2400 | 198.22 |

OUTPUT UNITS = WEIGHT FRACTIONS

| CONVERSION | | | MONOMER MIX | INSTANTANEOUS POLYMER | CUMULATIVE POLYMER |
|---|---|---|---|---|---|
| 0.000 | MONOMER | 1 | 0.2200 | 0.2835 | 0.2835 |
| | MONOMER | 2 | 0.7700 | 0.7060 | 0.7060 |
| | MONOMER | 3 | 0.0100 | 0.0106 | 0.0106 |
| 0.100 | MONOMER | 1 | 0.2133 | 0.2769 | 0.2803 |
| | MONOMER | 2 | 0.7768 | 0.7126 | 0.7092 |
| | MONOMER | 3 | 0.0099 | 0.0105 | 0.0106 |
| 0.200 | MONOMER | 1 | 0.2058 | 0.2694 | 0.2768 |
| | MONOMER | 2 | 0.7843 | 0.7201 | 0.7127 |
| | MONOMER | 3 | 0.0099 | 0.0105 | 0.0105 |
| 0.300 | MONOMER | 1 | 0.1973 | 0.2607 | 0.2729 |
| | MONOMER | 2 | 0.7929 | 0.7288 | 0.7166 |
| | MONOMER | 3 | 0.0098 | 0.0105 | 0.0105 |
| 0.400 | MONOMER | 1 | 0.1876 | 0.2507 | 0.2686 |
| | MONOMER | 2 | 0.8028 | 0.7389 | 0.7209 |
| | MONOMER | 3 | 0.0097 | 0.0104 | 0.0105 |
| 0.500 | MONOMER | 1 | 0.1761 | 0.2386 | 0.2639 |
| | MONOMER | 2 | 0.8144 | 0.7511 | 0.7256 |
| | MONOMER | 3 | 0.0095 | 0.0103 | 0.0105 |
| 0.600 | MONOMER | 1 | 0.1623 | 0.2237 | 0.2585 |

TABLE II-continued

Ternary Copolymer Kinetics for AA/NaA/EGDMA

| | | | | | |
|---|---|---|---|---|---|
| | MONOMER | 2 | 0.8284 | 0.7661 | 0.7311 |
| | MONOMER | 3 | 0.0093 | 0.0102 | 0.0104 |
| 0.700 | MONOMER | 1 | 0.1449 | 0.2043 | 0.2522 |
| | MONOMER | 2 | 0.8460 | 0.7857 | 0.7374 |
| | MONOMER | 3 | 0.0091 | 0.0100 | 0.0104 |
| 0.800 | MONOMER | 1 | 0.1216 | 0.1770 | 0.2446 |
| | MONOMER | 2 | 0.8698 | 0.8133 | 0.7451 |
| | MONOMER | 3 | 0.0087 | 0.0098 | 0.0103 |
| 0.900 | MONOMER | 1 | 0.0862 | 0.1324 | 0.2349 |
| | MONOMER | 2 | 0.9060 | 0.8585 | 0.7549 |
| | MONOMER | 3 | 0.0078 | 0.0091 | 0.0102 |
| 0.990 | MONOMER | 1 | 0.0195 | 0.0337 | 0.2220 |
| | MONOMER | 2 | 0.9758 | 0.9603 | 0.7679 |
| | MONOMER | 3 | 0.0047 | 0.0060 | 0.0101 |

TABLE III

Ternary Copolymer Kinetics for AA/NaA/MBAM

Starting Composition: 22/77/1:AA/NaA/MBAM

| MONOMER NAME | Q | E | Molecular Weight |
|---|---|---|---|
| MONO 1 AA | 1.1500 | 0.7700 | 72.05 |
| MONO 2 NAA | 0.7100 | −0.1200 | 94.05 |
| MONO 3 MBAM | 0.7400 | 1.0000 | 154.17 |

OUTPUT UNITS = WEIGHT FRACTIONS

| CONVERSION | | | MONOMER MIX | INSTANTANEOUS POLYMER | CUMULATIVE POLYMER |
|---|---|---|---|---|---|
| 0.000 | MONOMER | 1 | 0.2200 | 0.2836 | 0.2836 |
| | MONOMER | 2 | 0.7700 | 0.7082 | 0.7082 |
| | MONOMER | 3 | 0.0100 | 0.0082 | 0.0082 |
| 0.100 | MONOMER | 1 | 0.2133 | 0.2770 | 0.2804 |
| | MONOMER | 2 | 0.7765 | 0.7147 | 0.7113 |
| | MONOMER | 3 | 0.0102 | 0.0084 | 0.0083 |
| 0.200 | MONOMER | 1 | 0.2058 | 0.2694 | 0.2768 |
| | MONOMER | 2 | 0.7838 | 0.7220 | 0.7148 |
| | MONOMER | 3 | 0.0104 | 0.0086 | 0.0084 |
| 0.300 | MONOMER | 1 | 0.1973 | 0.2607 | 0.2730 |
| | MONOMER | 2 | 0.7921 | 0.7303 | 0.7185 |
| | MONOMER | 3 | 0.0106 | 0.0089 | 0.0085 |
| 0.400 | MONOMER | 1 | 0.1875 | 0.2506 | 0.2687 |
| | MONOMER | 2 | 0.8016 | 0.7401 | 0.7227 |
| | MONOMER | 3 | 0.0109 | 0.0093 | 0.0087 |
| 0.500 | MONOMER | 1 | 0.1761 | 0.2385 | 0.2639 |
| | MONOMER | 2 | 0.8127 | 0.7518 | 0.7273 |
| | MONOMER | 3 | 0.0112 | 0.0097 | 0.0088 |
| 0.600 | MONOMER | 1 | 0.1623 | 0.2235 | 0.2585 |
| | MONOMER | 2 | 0.8262 | 0.7663 | 0.7325 |
| | MONOMER | 3 | 0.0115 | 0.0101 | 0.0090 |
| 0.700 | MONOMER | 1 | 0.1449 | 0.2041 | 0.2522 |
| | MONOMER | 2 | 0.8432 | 0.7852 | 0.7386 |
| | MONOMER | 3 | 0.0119 | 0.0107 | 0.0092 |
| 0.800 | MONOMER | 1 | 0.1217 | 0.1769 | 0.2446 |
| | MONOMER | 2 | 0.8660 | 0.8117 | 0.7460 |
| | MONOMER | 3 | 0.0122 | 0.0115 | 0.0094 |
| 0.900 | MONOMER | 1 | 0.0865 | 0.1325 | 0.2348 |
| | MONOMER | 2 | 0.9009 | 0.8551 | 0.7555 |
| | MONOMER | 3 | 0.0125 | 0.0125 | 0.0097 |
| 0.990 | MONOMER | 1 | 0.0199 | 0.0343 | 0.2220 |
| | MONOMER | 2 | 0.9695 | 0.9537 | 0.7680 |
| | MONOMER | 3 | 0.0106 | 0.0120 | 0.0100 |

TABLE IV

Chemical Sequence Distribution (Diads and Triads) for AA/NaA/MBAM as a function of conversion.

MONOMER A = Acrylic Acid
MONOMER B = Sodium Acrylate
MONOMER C = N-N'-Methylene bis Acrylamide

SEQUENCE DISTRIBUTION
OUTPUT AT 0.000 CONVERSION

DYAD FRACTIONS

AA = 0.07954    BB = 0.38872    CC = 0.00001
AB + BA = 0.52257    AC + CA = 0.00182    BC + CB = 0.00734

TRIAD FRACTIONS

A-CENTERED TOTAL = 0.34174

| | | |
|---|---|---|
| AAA = 0.01851 | BAB = 0.19977 | CAC = 0.00000 |
| AAB + BAA = 0.12163 | AAC + CAA = 0.00042 | BAC + CAB = 0.00139 |

B-CENTERED TOTAL = 0.65367

| | | |
|---|---|---|
| ABA = 0.10444 | BBB = 0.23116 | CBC = 0.00002 |
| ABB + BBA = 0.31075 | ABC + CBA = 0.00294 | BBC + CBB = 0.00437 |

C-CENTERED TOTAL = 0.00459

TABLE IV-continued

| ACA = 0.00018 | BCB = 0.00294 | CCC = 0.00000 |
|---|---|---|
| ACB + BCA = 0.00146 | ACC + CCA = 0.00000 | BCC + CCB = 0.00002 |

NUMBER DENSITY & MOL (OR WT) FRACTION DISTRIBUTIONS

| LENGTH | A SEQUENCES N.D. | A SEQUENCES W.F. | B SEQUENCES N.D. | B SEQUENCES W.F. | C SEQUENCES N.D. | C SEQUENCES W.F. |
|---|---|---|---|---|---|---|
| 1 | 0.767 | 0.167 | 0.405 | 0.116 | 0.998 | 0.008 |
| 2 | 0.179 | 0.078 | 0.241 | 0.138 | 0.002 | 0.000 |
| 3 | 0.042 | 0.027 | 0.143 | 0.123 | 0.000 | 0.000 |
| 4 | 0.010 | 0.008 | 0.085 | 0.098 | 0.000 | 0.000 |
| 5 | 0.002 | 0.002 | 0.051 | 0.073 | 0.000 | 0.000 |
| 6 | 0.001 | 0.001 | 0.030 | 0.052 | 0.000 | 0.000 |
| 7 | 0.000 | 0.000 | 0.018 | 0.036 | 0.000 | 0.000 |
| 8 | 0.000 | 0.000 | 0.011 | 0.024 | 0.000 | 0.000 |
| 9 | 0.000 | 0.000 | 0.006 | 0.016 | 0.000 | 0.000 |
| 10 | 0.000 | 0.000 | 0.004 | 0.011 | 0.000 | 0.000 |
| 15 | 0.000 | 0.000 | 0.000 | 0.001 | 0.000 | 0.000 |
| 20 | 0.000 | 0.000 | 0.000 | 0.000 | 0.000 | 0.000 |

SEQUENCE DISTRIBUTION OUTPUT AT 0.300 CONVERSION

DYAD FRACTIONS

| AA = 0.07305 | BB = 0.40570 | CC = 0.00001 |
|---|---|---|
| AB + BA = 0.51163 | AC + CA = 0.00181 | BC + CB = 0.00779 |

TRIAD FRACTIONS

A-CENTERED TOTAL = 0.32962

| AAA = 0.01618 | BAB = 0.19835 | CAC = 0.00000 |
|---|---|---|
| AAB + BAA = 0.11329 | AAC + CAA = 0.00040 | BAC + CAB = 0.00141 |

B-CENTERED TOTAL = 0.66556

| ABA = 0.09837 | BBB = 0.24741 | CBC = 0.00002 |
|---|---|---|
| ABB + BBA = 0.31201 | ABC + CBA = 0.00300 | BBC + CBB = 0.00475 |

C-CENTERED TOTAL = 0.00481

| ACA = 0.00017 | BCB = 0.00315 | CCC = 0.00000 |
|---|---|---|
| ACB + BCA = 0.00147 | ACC + CCA = 0.00000 | BCC + CCB = 0.00002 |

NUMBER DENSITY & MOL (OR WT) FRACTION DISTRIBUTIONS

| LENGTH | A SEQUENCES N.D. | A SEQUENCES W.F. | B SEQUENCES N.D. | B SEQUENCES W.F. | C SEQUENCES N.D. | C SEQUENCES W.F. |
|---|---|---|---|---|---|---|
| 1 | 0.779 | 0.165 | 0.390 | 0.109 | 0.998 | 0.008 |
| 2 | 0.172 | 0.073 | 0.238 | 0.133 | 0.002 | 0.000 |
| 3 | 0.038 | 0.024 | 0.145 | 0.122 | 0.000 | 0.000 |
| 4 | 0.008 | 0.007 | 0.088 | 0.099 | 0.000 | 0.000 |
| 5 | 0.002 | 0.002 | 0.054 | 0.076 | 0.000 | 0.000 |
| 6 | 0.000 | 0.001 | 0.033 | 0.055 | 0.000 | 0.000 |
| 7 | 0.000 | 0.000 | 0.020 | 0.039 | 0.000 | 0.000 |
| 8 | 0.000 | 0.000 | 0.012 | 0.027 | 0.000 | 0.000 |
| 9 | 0.000 | 0.000 | 0.007 | 0.019 | 0.000 | 0.000 |
| 10 | 0.000 | 0.000 | 0.005 | 0.013 | 0.000 | 0.000 |
| 15 | 0.000 | 0.000 | 0.000 | 0.002 | 0.000 | 0.000 |
| 20 | 0.000 | 0.000 | 0.000 | 0.000 | 0.000 | 0.000 |

SEQUENCE DISTRIBUTION OUTPUT AT 0.600 CONVERSION

DYAD FRACTIONS

| AA = 0.06474 | BB = 0.42950 | CC = 0.00001 |
|---|---|---|
| AB + BA = 0.49556 | AC + CA = 0.00179 | BC + CB = 0.00840 |

TRIAD FRACTIONS

A-CENTERED TOTAL = 0.31308

| AAA = 0.01336 | BAB = 0.19568 | CAC = 0.00000 |
|---|---|---|
| AAB + BAA = 0.10225 | AAC + CAA = 0.00037 | BAC + CAB = 0.00141 |

B-CENTERED TOTAL = 0.68182

| ABA = 0.09013 | BBB = 0.27083 | CBC = 0.00003 |
|---|---|---|
| ABB + BBA = 0.31248 | ABC + CBA = 0.00306 | BBC + CBB = 0.00530 |

C-CENTERED TOTAL = 0.00511

| ACA = 0.00016 | BCB = 0.00346 | CCC = 0.00000 |
|---|---|---|
| ACB + BCA = 0.00147 | ACC + CCA = 0.00000 | BCC + CCB = 0.00002 |

NUMBER DENSITY & MOL (OR WT) FRACTION DISTRIBUTIONS

| LENGTH | A SEQUENCES N.D. | A SEQUENCES W.F. | B SEQUENCES N.D. | B SEQUENCES W.F. | C SEQUENCES N.D. | C SEQUENCES W.F. |
|---|---|---|---|---|---|---|
| 1 | 0.794 | 0.163 | 0.369 | 0.100 | 0.998 | 0.009 |
| 2 | 0.164 | 0.067 | 0.233 | 0.126 | 0.002 | 0.000 |
| 3 | 0.034 | 0.021 | 0.147 | 0.119 | 0.000 | 0.000 |
| 4 | 0.007 | 0.006 | 0.093 | 0.100 | 0.000 | 0.000 |
| 5 | 0.001 | 0.001 | 0.058 | 0.079 | 0.000 | 0.000 |
| 6 | 0.000 | 0.000 | 0.037 | 0.060 | 0.000 | 0.000 |
| 7 | 0.000 | 0.000 | 0.023 | 0.044 | 0.000 | 0.000 |
| 8 | 0.000 | 0.000 | 0.015 | 0.032 | 0.000 | 0.000 |
| 9 | 0.000 | 0.000 | 0.009 | 0.022 | 0.000 | 0.000 |
| 10 | 0.000 | 0.000 | 0.006 | 0.016 | 0.000 | 0.000 |
| 15 | 0.000 | 0.000 | 0.001 | 0.002 | 0.000 | 0.000 |
| 20 | 0.000 | 0.000 | 0.000 | 0.000 | 0.000 | 0.000 |

SEQUENCE DISTRIBUTION OUTPUT AT 0.900 CONVERSION

DYAD FRACTIONS

| AA = 0.05230 | BB = 0.47044 | CC = 0.00001 |
|---|---|---|
| AB + BA = 0.46618 | AC + CA = 0.00171 | BC + CB = 0.00935 |

TRIAD FRACTIONS

A-CENTERED TOTAL = 0.28546

| AAA = 0.00953 | BAB = 0.18928 | CAC = 0.00000 |
|---|---|---|
| AAB + BAA = 0.08495 | AAC + CAA = 0.00031 | BAC + CAB = 0.00139 |

B-CENTERED TOTAL = 0.70900

| ABA = 0.07680 | BBB = 0.31285 | CBC = 0.00003 |
|---|---|---|
| ABB + BBA = 0.31002 | ABC + CBA = 0.00308 | BBC + CBB = 0.00622 |

C-CENTERED TOTAL = 0.00553

| ACA = 0.00013 | BCB = 0.00394 | CCC = 0.00000 |
|---|---|---|
| ACB + BCA = 0.00144 | ACC + CCA = 0.00000 | BCC + CCB = 0.00002 |

NUMBER DENSITY & MOL (OR WT) FRACTION DISTRIBUTIONS

| LENGTH | A SEQUENCES N.D. | A SEQUENCES W.F. | B SEQUENCES N.D. | B SEQUENCES W.F. | C SEQUENCES N.D. | C SEQUENCES W.F. |
|---|---|---|---|---|---|---|
| 1 | 0.818 | 0.157 | 0.335 | 0.085 | 0.998 | 0.010 |
| 2 | 0.149 | 0.057 | 0.223 | 0.113 | 0.002 | 0.000 |
| 3 | 0.027 | 0.016 | 0.148 | 0.112 | 0.000 | 0.000 |
| 4 | 0.005 | 0.004 | 0.099 | 0.100 | 0.000 | 0.000 |
| 5 | 0.001 | 0.001 | 0.066 | 0.083 | 0.000 | 0.000 |
| 6 | 0.000 | 0.000 | 0.044 | 0.066 | 0.000 | 0.000 |
| 7 | 0.000 | 0.000 | 0.029 | 0.051 | 0.000 | 0.000 |
| 8 | 0.000 | 0.000 | 0.019 | 0.039 | 0.000 | 0.000 |
| 9 | 0.000 | 0.000 | 0.013 | 0.029 | 0.000 | 0.000 |
| 10 | 0.000 | 0.000 | 0.009 | 0.022 | 0.000 | 0.000 |
| 15 | 0.000 | 0.000 | 0.001 | 0.004 | 0.000 | 0.000 |
| 20 | 0.000 | 0.000 | 0.000 | 0.001 | 0.000 | 0.000 |

SEQUENCE DISTRIBUTION OUTPUT AT 0.990 CONVERSION

DYAD FRACTIONS

| AA = 0.04565 | BB = 0.49584 | CC = 0.00001 |
|---|---|---|
| AB + BA = 0.44716 | AC + CA = 0.00162 | BC + CB = 0.00972 |

TRIAD FRACTIONS

A-CENTERED TOTAL = 0.26768

| AAA = 0.00765 | BAB = 0.18348 | CAC = 0.00000 |
|---|---|---|
| AAB + BAA = 0.07494 | AAC + CAA = 0.00027 | BAC + CAB = 0.00133 |

B-CENTERED TOTAL = 0.72669

| ABA = 0.06924 | BBB = 0.34058 | CBC = 0.00003 |
|---|---|---|
| ABB + BBA = 0.30715 | ABC + CBA = 0.00301 | BBC + CBB = 0.00668 |

C-CENTERED TOTAL = 0.00563

| ACA = 0.00011 | BCB = 0.00412 | CCC = 0.00000 |
|---|---|---|
| ACB + BCA = 0.00137 | ACC + CCA = 0.00000 | BCC + CCB = 0.00002 |

NUMBER DENSITY & MOL (OR WT) FRACTION DISTRIBUTIONS

| LENGTH | A SEQUENCES N.D. | A SEQUENCES W.F. | B SEQUENCES N.D. | B SEQUENCES W.F. | C SEQUENCES N.D. | C SEQUENCES W.F. |
|---|---|---|---|---|---|---|
| 1 | 0.832 | 0.154 | 0.313 | 0.075 | 0.998 | 0.010 |
| 2 | 0.140 | 0.052 | 0.215 | 0.103 | 0.002 | 0.000 |
| 3 | 0.023 | 0.013 | 0.148 | 0.107 | 0.000 | 0.000 |
| 4 | 0.004 | 0.003 | 0.101 | 0.098 | 0.000 | 0.000 |

TABLE IV-continued

| 5 | 0.001 | 0.001 | 0.070 | 0.084 | 0.000 | 0.000 |
| 6 | 0.000 | 0.000 | 0.048 | 0.069 | 0.000 | 0.000 |
| 7 | 0.000 | 0.000 | 0.033 | 0.055 | 0.000 | 0.000 |
| 8 | 0.000 | 0.000 | 0.023 | 0.043 | 0.000 | 0.000 |
| 9 | 0.000 | 0.000 | 0.016 | 0.034 | 0.000 | 0.000 |
| 10 | 0.000 | 0.000 | 0.011 | 0.026 | 0.000 | 0.000 |
| 15 | 0.000 | 0.000 | 0.002 | 0.006 | 0.000 | 0.000 |
| 20 | 0.000 | 0.000 | 0.000 | 0.001 | 0.000 | 0.000 |

TABLE V

| BINARY REACTIVITY RATIOS | |
| --- | --- |
| BINARY REACTION | REACTIVITY RATIOS |
| 1 ACRYLIC ACID | $R1 = 0.8162$ |
| 2 SODIUM ACRYLATE | $R2 = 0.5549$ |
| 1 ACRYLIC ACID | $R1' = 1.8552$ |
| 2 MBAM | $R2' = 0.5113$ |
| 1 SODIUM ACRYLATE | $R1'' = 0.8388$ |
| 2 MBAM | $R2'' = 0.3401$ |

Additional advantages and modifications will readily occur to those skilled in the art. The invention in its broader aspects is, therefore, not limited to the specific details, representative apparatus and illustrative examples shown and described. Accordingly, departures may be made from such details without departing from the spirit and scope of the general inventive concept as defined by the appended claims and their equivalents.

What is claimed is:

1. A process relating to polymer production wherein, with the aid of a digital computer, stable polymeric substances are simulated by empirical functions, an appropriate polymer having useful properties of size, shape, composition, volume, stiffness, and polymer structure is selected from said simulated polymeric substances, and a useful polymer is produced, comprising
   providing the computer with a data base of polymer molecular connectivities of polymeric substances,
   from the molecular connecivities selecting information to form a monomer and determining chemical composition through estimation of individual polymer chain chemical composition,
   calculating by statistical thermodynamics the shape of three-dimensional folding large molecules of the polymeric substances,
   assembling the resulting 3-dimensionally folded molecular chemical composition into a proposed polymeric cluster of the polymeric substances,
   visually displaying by computer generated graphics or pictures said polymeric clusters,
   estimating at least one of the physical properties of size, shape, composition, volume, stiffness or polymer structure of the resulting proposed displayed polymeric cluster,
   choosing a proposed polymeric cluster having at least one useful physical property,
   producing said selected cluster by synthesizing the resulting polymeric product by a format,
   wherein the estimated physical property of the simulated cluster of the polymeric substance is related to the resulting polymer product.

2. The process of claim 1, wherein a physical property, i.e. the effect of a solvent, on the molecular chain chemical composition and 3-dimensional folding is estimated through In Situ optimization.

3. The process of claim 1, wherein said assembling step further comprises use of molecular excluded volume constraints determined by vector geometry.

4. The process of claim 1, wherein said assembling step further comprises iterative use of numerical methods.

5. The process of claim 1, wherein said polymer product is a plastic, packaging material, optical disc material, barrier membrane, adhesive, viscosity improver, dispersant, electronic chemical, coating, or synthetic biopolymer.

6. The process of claim 1, wherein said polymer product is a polymer blend compatibilizer, high temperature plastic, thermoplastic polymer, thermoplastic polymer blend, elastomeric polymer, elastomeric polymer blend, amorphous polymer, amorphous polymer blend, crystalline polymer, crystalline polymer blend, liquid crystalline polymer or liquid crystalline polymer blend.

7. The process of claim 1, wherein said polymer product is a barrier membrane formed from bio-separator material.

8. A process relating to polymer production as claimed in claim 1 wherein said polymeric substance is a copolymeric substance.

9. A process relating to polymer production as claimed in claim 1 wherein in the calculation by the method of statistical thermodynamics the polymeric substance has greater than five (5) monomer units.

10. A process relating to polymer production as claimed in claim 1,
    wherein determining chemical composition through a estimation of individual polymer chain composition comprises
    a function of conversion and reaction time using chemical kinetics rate expressions.

11. A process relating to polymer properties as claimed in claim 1
    wherein said calculating by the method of statistical thermodynamics comprises a numerical method.

12. In the process as claimed in claim 1 the step of developing a format for synthesizing the resulting and related polymer product.

13. A process relating to polymer production by identification of polymeric substances by empirical functions to simulate final stable polymeric substances,
    with the aid of a digital computer,
    comprising providing the computer with a data base of polymer molecular connectivities of polymeric substances,
    from the molecular connectivities selecting information to form a monomer and determining chemical composition through estimation of individual polymer chain chemical compositions,
    calculating by a method of statistical thermodynamics the shape of three-dimensional folding large molecules of the polymeric substances,
    assembling the resulting 3-dimensionally folded molecular chemical composition into a proposed polymeric cluster of the polymeric substances,
    visually displaying, using computer graphics, the computer generated picture of the resulting polymeric cluster,
    evaluating properties of the resulting displayed polymeric cluster,
    using said properties of the visually displayed polymeric cluster to select an appropriate polymer product,
    and synthesizing said selected appropriate polymer product by a format for synthesizing said polymer product, wherein the produced polymer product has at least one related property to the graphically displayed and selected proposed polymeric structure, whereby final stable polymeric substances are simulated and produced.

14. A process relating to polymeric production as claimed in claim 13, wherein said polymeric substance is a copolymeric substance.

15. A process relating to polymer production as claimed in claim 13, wherein in the calculation by the method of statistical thermodynamics the polymeric substance has greater than five (5) monomer units.

16. A process relating to polymer production as claimed in claim 13,
wherein determining chemical composition through an estimation of individual polymer chain composition comprises
a function of conversion and reaction time using chemical kinetics rate expressions.

17. A process relating to polymer properties as claimed in claim 13
wherein said calculating by the method of statistical thermodynamics comprises a numerical method.

* * * * *